(12) United States Patent
Hansen et al.

(10) Patent No.: US 10,561,618 B2
(45) Date of Patent: Feb. 18, 2020

(54) ORALLY AVAILABLE PHARMACEUTICAL FORMULATION SUITABLE FOR IMPROVED MANAGEMENT OF MOVEMENT DISORDERS

(71) Applicant: Contera Pharma ApS, Copenhagen K (DK)

(72) Inventors: John Bondo Hansen, Jyderup (DK); Mikael S. Thomsen, Hvidovre (DK); Jens D. Mikkelsen, Lyngby (DK); Peter Gudmund Nielsen, Værløse (DK); Mads Kreilgaard, Farum (DK)

(73) Assignee: Contera Pharma ApS, Copenhagen K (DK)

(*) Notice: Subject to any disclaimer, the term of this patent is extended or adjusted under 35 U.S.C. 154(b) by 505 days.

(21) Appl. No.: 14/395,134

(22) PCT Filed: Apr. 18, 2013

(86) PCT No.: PCT/DK2013/050111
§ 371 (c)(1),
(2) Date: Oct. 17, 2014

(87) PCT Pub. No.: WO2013/156035
PCT Pub. Date: Oct. 24, 2013

(65) Prior Publication Data
US 2015/0104506 A1    Apr. 16, 2015

(30) Foreign Application Priority Data

Apr. 18, 2012 (DK) .................................. 2012 70196
Jun. 1, 2012 (WO) ................. PCT/DK2012/050190
Dec. 4, 2012 (DK) .................................. 2012 70755

(51) Int. Cl.
*A61K 9/24* (2006.01)
*A61K 31/506* (2006.01)
(Continued)

(52) U.S. Cl.
CPC ............ *A61K 9/209* (2013.01); *A61K 9/0053* (2013.01); *A61K 9/20* (2013.01); *A61K 9/2009* (2013.01);
(Continued)

(58) Field of Classification Search
None
See application file for complete search history.

(56) References Cited

U.S. PATENT DOCUMENTS 3,717,634 A    2/1973  Wu et al.
3,976,776 A    8/1976  Wu et al.
(Continued)

FOREIGN PATENT DOCUMENTS

DE    10353657      6/2005
WO    WO-2000006161 2/2000
(Continued)

OTHER PUBLICATIONS

Avital, A. et al., Zolmitriptan compared to propranolol in the treatment of acute neuroleptic-induced akathisia: A comparative double-blind study, *European Neuropsychopharmacology*, 19(7): 476-482, Jul. 1, 2009.
(Continued)

*Primary Examiner* — Jianfeng Song
(74) *Attorney, Agent, or Firm* — Julie K. Staple; Dinsmore & Shohl LLP

(57) ABSTRACT

The present invention provides a pharmaceutical formulation for oral administration comprising an agonist of two or more of the 5-HT1B, 5-HT1D and 5-HT1F receptors, such as a triptan, e.g. zolmitriptan, in a matrix constituent with extended release characteristics, and further comprising a 5-HT1A-R agonist, such as buspirone, in a constituent with immediate-release characteristics. The special formulation is particularly well-suited for use in the treatment of movement
(Continued)

disorders by combining the two active ingredients in a manner that achieves synergy from both the combination per se and the special release parameters of the pharmaceutical formulation, allowing for ease of administration and reducing the risk of adverse effects of each of the two active ingredients.

39 Claims, 9 Drawing Sheets

(51) Int. Cl.
    *A61K 9/20*       (2006.01)
    *A61K 31/198*    (2006.01)
    *A61K 31/165*    (2006.01)
    *A61K 9/00*       (2006.01)
    *A61K 31/422*    (2006.01)
    *A61K 9/48*       (2006.01)
    *A61K 45/06*     (2006.01)
    *A61K 31/216*    (2006.01)
    *A61K 31/454*    (2006.01)
    *A61K 9/28*       (2006.01)
    *A61K 9/50*       (2006.01)
    *A61K 31/496*    (2006.01)
    *A61K 31/505*    (2006.01)
    *A61K 31/4545*   (2006.01)

(52) U.S. Cl.
    CPC .......... *A61K 9/2054* (2013.01); *A61K 9/2866* (2013.01); *A61K 9/485* (2013.01); *A61K 9/4808* (2013.01); *A61K 9/4866* (2013.01); *A61K 9/5084* (2013.01); *A61K 31/165* (2013.01); *A61K 31/198* (2013.01); *A61K 31/216* (2013.01); *A61K 31/422* (2013.01); *A61K 31/454* (2013.01); *A61K 31/4545* (2013.01); *A61K 31/496* (2013.01); *A61K 31/505* (2013.01); *A61K 31/506* (2013.01); *A61K 45/06* (2013.01)

(56) References Cited

U.S. PATENT DOCUMENTS

| | | | |
|---|---|---|---|
| 4,166,452 A | 9/1979 | Generates, Jr. | |
| 4,182,763 A | 1/1980 | Casten et al. | |
| 4,265,874 A | 5/1981 | Bonsen et al. | |
| 4,356,108 A | 10/1982 | Schwab et al. | |
| 4,438,119 A | 3/1984 | Allen et al. | |
| 4,640,921 A | 2/1987 | Othmer et al. | |
| 4,687,772 A | 8/1987 | Alderdice | |
| 4,777,173 A | 10/1988 | Shrotryia et al. | |
| 5,185,329 A | 2/1993 | Gawin et al. | |
| 5,288,501 A * | 2/1994 | Nurnberg | A61K 9/2095 |
| | | | 424/465 |
| 5,431,922 A | 7/1995 | Nicklasson | |
| 5,466,699 A | 11/1995 | Robertson et al. | |
| 5,484,788 A | 1/1996 | Sharpe et al. | |
| 5,633,009 A | 5/1997 | Kenealy et al. | |
| 5,637,314 A | 6/1997 | Sharpe et al. | |
| 5,705,506 A | 1/1998 | Merlet et al. | |
| 6,150,365 A | 11/2000 | Mayol | |
| 6,432,956 B1 | 8/2002 | Dement et al. | |
| 6,750,237 B1 | 6/2004 | Dearn et al. | |
| 7,220,767 B2 | 5/2007 | Dearn et al. | |
| 7,470,435 B2 * | 12/2008 | Dixit | A61K 9/1676 |
| | | | 424/451 |
| 8,329,734 B2 | 12/2012 | Aung-Din | |
| 2006/0003005 A1 * | 1/2006 | Cao | A61K 9/2081 |
| | | | 424/470 |
| 2007/0173536 A1 | 7/2007 | Van Der Schaaf et al. | |
| 2007/0249621 A1 | 10/2007 | Wolf et al. | |
| 2007/0270449 A1 * | 11/2007 | Barlow | A61K 31/135 |
| | | | 514/282 |
| 2008/0069874 A1 * | 3/2008 | Hall | A61K 45/06 |
| | | | 424/464 |
| 2008/0125413 A1 * | 5/2008 | Burgey | C07D 401/14 |
| | | | 514/221 |
| 2008/0166407 A1 * | 7/2008 | Shalaby | A61K 9/2031 |
| | | | 424/465 |
| 2010/0105783 A1 | 4/2010 | Lee et al. | |
| 2011/0318321 A1 | 12/2011 | Selva et al. | |

FOREIGN PATENT DOCUMENTS

| | | | |
|---|---|---|---|
| WO | WO-2002/044159 | 6/2002 | |
| WO | WO-2003011255 | 2/2003 | |
| WO | WO-2003024960 | 3/2003 | |
| WO | WO-2005034908 | 4/2005 | |
| WO | WO-2006/027681 | 3/2006 | |
| WO | WO-2007-129329 | * 11/2007 | |
| WO | WO-2007144422 | 12/2007 | |
| WO | WO-2008047839 | 4/2008 | |
| WO | WO-2009118167 | 10/2009 | |
| WO | WO-2009/156380 | 12/2009 | |
| WO | WO-2010/044736 | 4/2010 | |
| WO | WO-2011/079313 | 6/2011 | |
| WO | WO-2012/048710 | 4/2012 | |
| WO | WO-2002/053139 | 7/2012 | |
| WO | WO-2012/0163365 | 12/2012 | |

OTHER PUBLICATIONS

Bara-Jimenez Et al., Effects of serotonin 5-HT1A agonist in advanced Parkinson's disease. Movement Disorders vol. 20, No. 8, 2005, pp. 932-936.
Blackburn, T., Serotonergic agents and Parkinson's disease, *Drug Discovery Today: Therapeutic Strategies*, 1(1): 35-41, Sep. 2004.
Bonifati, V. et al., Buspirone in levodopa-induced dyskinesias, *Clin NeurPharmacol*, 17(1): 73-82, 1994.
Carta et al., Dopamine released from 5-HT terminals is the cause of L-DOPA-induced dyskinesia in Parkinsonian rats, *Brain*, 130(7): 1819-1833, Jul. 1, 2007.
Dekundy, A. et al., Modulation of I-DOPA-induced abnormal involuntary movements by clinically tested compounds: Further validation of the rat dyskinesia model, *Behavioural Brain Research*, 179: 76-89, 2007.
Del Sorbo, F. et al., Levodopa-induced dyskinesias and their management, *J Neurol*, 255 Suppl 4: 32-41, 2008.
Elangbam, C. et al., 5-Hydroxytryptamine (5HT) Receptors in the Heart Valves of Cynomolgus Monkeys and Sprague-Dawley Rats, *J Histochem Cytochem*, 53(5):671-677, 2005.
Filip, M. et al., Overview on 5-HT receptors and their role in physiology and pathology of the central nervous system, *Pharmacol. Reports*. 61, 761-777, 2009.
Fox, S. et al., Serotonin and Parkinson's Disease: On Movement, Mood, and Madness, *Movement Disorders*, 24(9): 1255-66, 2009.
Gerlach, M. et al. Anti-dyskinetic effects of flibanserin on levodopa-induced dyskinesia in the 6-hydroxydopamine-lesioned rat model of Parkinson's disease. Poster presentations/Parkinsonism and related disorders 15S2 (2009) S29-S199.
Goetz et al., Sarotozan as a treatment for dyskinesias in Parkinson's disease: A double-blind placebo-controlled trial. Movement Disorders vol. 22, No. 2, 2007, pp. 179-186.
Gregoire, L. et al., Low doses of sarizotan reduce dyskinesias and maintain antiparkinsonian efficacy of L-Dopa in parkinsonian monkeys, Parkinsonism Relat Disord., 5(6): 445-52, 2009.
Jackson, M. et al., Effect of 5-HT1B/D receptor agonist and antagonist administration on motor function in haloperidol and MPTP-treated common marmosets, Pharmacology Biochemistry and Behavior, 79(3): 391-400, Nov. 1, 2004.
Jenner, P., Molecular mechanisms of L-DOPA-induced dyskinesia, Nat Rev Neurosci, 9(9): 665-77, 2008.
Kalvass et al., Use of plasma and brain unbound fractions to assess the extent of brain distribution of 34 drugs: Comparison of unbound

(56) References Cited

OTHER PUBLICATIONS concentration ratios to in vivo P-Glycoprotein efflux ratios. Drug metabolism and distribution, 35:660-666, 2007.
Kirik, D. et al., Growth and Functional Efficacy of Intrastriatal Nigral Transplants Depend on the Extent of Nigrostriatal Degeneration, J. Neurosci, 21: 2889-96, 2001.
Ludwig, C. et al., Buspirone, Parkinson's Disease, and the locus ceruleus, *Clin Neuropharmacol.* 9(4):373-8, 1986.
Moss, L. et al., Buspirone in the treatment of tardive dyskinesia, *J Clin Psychopharmacol.*, 13(3): 204-9, Jun. 1993.
Muñoz, A. et al., Serotonin neuron-dependent and -independent reduction of dyskinesia by 5-HT1A and 5-HT1B receptor agonists in the rat Parkinson model, *Experimental Neurology*, 219: 298-307, 2009.
Muñoz, A. et al., Combined 5-HT1A and 5-HT1B receptor agonists for the treatment of L-DOPA-induced dyskinesia, Brain: A journal of Neurology, 131(12): 3380-94, Dec. 2008.
Newman-Tancredi, A., The importance of 5-HT1A receptor agonism in antipsychotic drug action: Rationale and perspectives, Current Opinion in Investigational Drugs, 11(7): 802-812, 2010.
Ohno, Y., New Insight into the Therapeutic Role of 5-HT1A Receptors in Central Nervous System Disorders, Central Nervous System Agents in Medicinal Chemistry, 10: 148-157, 2010.
Olsson, M. et al., Forelimb Akinesia in the Rat Parkinson Model: Differential Effects of Dopamine Agonists and Nigral Transplants as Assessed by a New Stepping Test, J Neurosci, 15:3863-75, 1995.
Rádl et al., Synthesis and analgesic activity of some deaza derivatives of anpirtoline. Arch. Pharm. Med. Chem. 332, 13-18 (1999).
Roppongi, T. et al., Perospirone in treatment of Huntington's disease: A first case report, Prog Neuropsychopharmacol Biol Psychiatry, 31(1):308-10, 2007.
Schallert, T. et al., A Clinically Relevant Unilateral Rat Model of Parkinsonian Akinesia, J. Neural TransplPlast, 3: 332-3, 1992.
Tfelt-Hansen., Does sumatriptan cross the blood-brain barrier in animals and man? J Headache Pain (2010) 11:5-12.
Tomiyama M. et al., A serotonin 5-HT1A receptor agonist prevents behavioral sensitization to L-DOPA in a rodent model of Parkinson's disease, Neuroscience Research, 52(2): 185-194, Jun. 1, 2005.
Uchiyama et al., Urinary dysfunction in early and untreated Parkinson's disease. J Neurol Neurosurg Psychiatry. 2011; 82(12): 1382-6).
Wall et al., Distribution of Zolmitriptan into the CNS in healthy volunteers. Drugs R D 2005; 6 (3): 139-147.
A concise explanation of the relevance of DE-10353657.
A concise explanation of the relevance of WO2008047839.
A concise explanation of the relevance of WO2009118167.

\* cited by examiner

ORALLY AVAILABLE PHARMACEUTICAL FORMULATION SUITABLE FOR IMPROVED MANAGEMENT OF MOVEMENT DISORDERS

FIELD OF INVENTION

The present invention relates to a pharmaceutical formulation comprising an agonist of two or more of the 5-HT1B, 5-HT1D and 5-HT1F receptors, such as a triptan, e.g. zolmitriptan, in a matrix constituent having extended release characteristics, and further comprising a 5-HT1A-R agonist, such as buspirone, in a constituent having immediate-release characteristics. The present formulation is particularly well-suited for use in the treatment of movement disorders and is suitable for oral administration.

BACKGROUND OF INVENTION

Movement disorders are a group of diseases that affect the ability to produce and control body movement, and are often associated with neurological disorders or conditions associated with neurological dysfunction. Movement disorders may manifest themselves in abnormal fluency or speed of movement, excessive or involuntary movement, or slowed or absent voluntary movement.

Movement disorders are frequently caused by impaired regulation of dopamine neurotransmission. Parkinson's disease (PD) is an example of a movement disorder associated with dysfunctional regulation of dopamine neurotransmission, which is caused by progressive degeneration of dopamine neurons. Tardive dyskinesia is another example of a movement disorder associated with dysfunctional regulation of dopamine neurotransmission.

In order to replace the lost dopamine, PD is currently treated with e.g. Levodopa (L-DOPA, a precursor of dopamine). Unfortunately, the treatment of PD with L-DOPA often gives rise to a specific type of dyskinesia called L-DOPA Induced Dyskinesia (LID) which is caused by excessive dopamine levels in the synapses.

Dopamine release and re-uptake is regulated by a number of neurotransmitters, including serotonin (5-HT). Serotonin acts by binding to a number of different serotonergic receptors, of which agonists and antagonists of some serotonergic receptors have been investigated for treatment of movement disorders.

Modulators of serotonin (5-HT) neurotransmission individually have been shown to ameliorate or prevent LID. One example thereof is sarizotan, which is a 5-HT1A agonist and a dopamine receptor antagonist (Grégoire et al: *Parkinsonism Relat Disord.* 2009; 15(6): 445-52). In a phase 2A study and in an open labeled study sarizotan reduced LID. However, in several large phase 2b studies no significant effects of sarizotan compared to placebo could be shown.

The effects of the 5-HT1A agonist buspirone on Parkinson's disease have been studied in a small open study (Ludwig et al: Clin Neuropharmacol. 1986; 9(4):373-8). It was found that doses (10-60 mg/day), which are normally used to treat patients suffering from anxiety, did not have any effects on Parkinson's disease or dyskinesia. At higher doses (100 mg/day) it was observed that buspirone reduced dyskinesia but with a significant worsening of disability ratings. This showed that high doses of buspirone could worsen the akinesia associated with Parkinson's disease.

Recently it has been shown that a combination of a 5-HT1A and of a 5-HT1B agonist increased efficacy in reducing LID in animal models (e.g. Muñoz et al: *Brain.* 2008; 131: 3380-94; Muñoz et al: *Experimental Neurology* 219 (2009) 298-307). The combined 5-HT1A and 5-HT1B agonist eltoprazine has also recently been suggested for treatment of LID (WO2009/156380). Eltoprazine is estimated to be equipotent in terms of activation of 5-HT1A and 5-HT1B receptors. The long term effects of the use of the compound for treatment are unknown.

5-HT1A agonists given in high doses can lead to the development of the serotonin syndrome or serotonin toxicity; a form of poisoning. Because of the severity of serotonin syndrome, it is therefore important to maintain a low exposure of the 5-HT1A agonist.

The present inventors have previously discovered that surprising synergistic effects arise from combining an agonist of two or more the 5-HT1B, 5-HT1D and 5-HT1F receptors, exemplified by zolmitriptan, with a 5-HT1A agonist, exemplified by buspirone, when assayed in an animal model for LID, thus effectively increasing the therapeutic index. While zolmitriptan generally fails to inhibit LID when administered alone, it proved effective in potentiating the effects of buspirone to inhibit LID—even at very low doses; i.e. doses of buspirone which alone failed to produce a significant effect on LID (WO2012/048710).

In PCT/DK2012/050190 (filed Jan. 6, 2012) and further provided herein, the present inventors have investigated administering zolmitriptan separately before administering buspirone and found additional beneficial effects by such sequential administration. In PCT/DK2012/050190 both compounds were administered by injections to achieve this further beneficial effect (s.c. or i.p.). However, repeated and timely separated injections are generally undesired especially for long-term treatments, and bolus injections may cause too-high plasma concentration doses which is a potential safety concern.

SUMMARY OF INVENTION

The present invention provides an orally available pharmaceutical formulation designed to obtain the beneficial synergistic effects of combining an agonist of two or more of the 5-HT1B, D and F receptors, exemplified by zolmitriptan, with a 5-HT1A agonist, exemplified by buspirone; surprisingly also achieving the additional beneficial effect of sequential administration of the two active ingredients, thus improving efficacy and reducing the risk of adverse effects while enabling ease of administration by eliminating the need for multiple administrations (such as injections or ingestions).

It is an aspect of the present invention to provide a pharmaceutical formulation comprising
  a. a matrix constituent comprising an active pharmaceutical ingredient being an agonist of two or more of the 5-HT1B, 5-HT1D and 5-HT1F receptors, said matrix constituent providing for extended release of said active pharmaceutical ingredient, and
  b. a constituent comprising an active pharmaceutical ingredient being an agonist of the 5-HT1A receptor, said constituent providing for immediate release of said active pharmaceutical ingredient.

In one embodiment said pharmaceutical formulation is a dosage form, such as a solid dosage form, such as a tablet. In one embodiment said dosage form comprises constituents a. and b. in separate compartments or layers; such as an inner core matrix and an outer coating; or a bi-layered tablet. In another embodiment, each of said constituents are provided together in a capsule, wherein said capsule comprises constituents a. and b. as separate granules or pellets.

In one embodiment, said agonist of two or more of the 5-HT1B, 5-HT1D and 5-HT1F receptors is a triptan, such as a triptan selected from the group consisting of zolmitriptan, rizatriptan, sumatriptan, naratriptan, almotriptan, frovatriptan, avitriptan, imotriptan and eletriptan.

In one embodiment, said agonist of the 5-HT1A receptor is selected from the group consisting of buspirone, tandospirone, gepirone, alnespirone, binospirone, ipsapirone, perospirone, befiradol, repinotan piclozotan, osemozotan, flesinoxan, flibanserin and sarizotan.

In one embodiment said matrix constituent a. comprises predetermined amounts of excipients, preferably release-controlling excipients, such as hydroxypropyl-methylcellulose (HPMC) and/or microcrystalline cellulose (MCC), and optionally further comprises talc, optionally being compressed to a suitable hardness, wherein said matrix constituent a. provides for a maximum release of the active pharmaceutical ingredient of more than 80%, such as more than 85%.

In one embodiment said constituent b., comprises an excipient, such as a film-forming excipient, which may in one embodiment be hydroxypropylmethylcellulose (HPMC).

The present pharmaceutical formulation provides for extended release of the agonist of two or more of the 5-HT1B, 5-HT1D and 5-HT1F receptors with a concomitant relatively constant or steady state plasma concentration thereof, and an immediate release of the agonist of the 5-HT1A receptor with a concomitant peak plasma concentration thereof.

In one embodiment, the pharmaceutical formulation comprises one or more further active ingredients, such as L-DOPA, carbidopa and/or benserazide.

It is an aspect of the present invention to provide the pharmaceutical formulation as defined herein for use in the treatment of a movement disorder, including Parkinson's disease, movement disorders associated with Parkinson's disease such as bradykinesia, akinesia and dyskinesia, L-DOPA induced dyskinesia, and tardive dyskinesia.

DEFINITIONS

The term "agonist" in the present context refers to a substance capable of binding to and activating a (one or more) receptor(s). A 5-HT1A receptor agonist (5-HT1A agonist) is thus capable of binding to and activating the 5-HT1A receptor. An agonist of two or more the 5-HT1B, 5-HT1D and 5-HT1F receptors (5-HT1B/D/F agonist) is capable of binding to and activating two or three of the 5-HT1B, 5-HT1D and 5-HT1F receptor. The terms '5-HT1 agonist', '5-HT1 receptor agonist', and 'agonist of the 5-HT1 receptor' are used interchangeably herein.

The term "antagonist" in the present context refers to a substance capable of inhibiting the effect of a receptor agonist.

The terms "dopamine," "DA" and "4-(2-aminoethyl)benzene-1,2-diol," refer to a catecholamine neurotransmitter and hormone. Dopamine is a precursor of adrenaline (epinephrine) and noradrenaline (norepinephrine) and activates the five types of dopamine receptors—D1, D2, D3, D4, and D5—and their variants.

"L-DOPA" or "3,4-dihydroxyphenylalanine" is a precursor to the neurotransmitters dopamine, norepinephrine (noradrenaline), and epinephrine (adrenaline). L-DOPA is able to cross the blood-brain barrier, and is converted to dopamine by the enzyme aromatic L-amino acid decarboxylase (AADC), also known as DOPA decarboxylase (DDC). L-DOPA is used for treatment of Parkinson's disease.

The terms "Parkinson's disease," "Parkinson's" and "PD" refer to a neurological syndrome characterized by a dopamine deficiency, resulting from degenerative, vascular, or inflammatory changes in the basal ganglia of the substantia nigra. This term also refers to a syndrome which resembles Parkinson's disease, but which may or may not be caused by Parkinson's disease, such as Parkinsonian-like side effects caused by certain antipsychotic drugs. Parkinson's disease is also referred to as paralysis agitans and shaking palsy.

The term "synapse" refers to an area of a neuron that permits said neuron to pass an electrical or chemical signal to another cell. In a synapse, a plasma membrane of the signal-passing neuron (the pre-synaptic neuron) comes into close apposition with the membrane of the target (post-synaptic) cell.

The term "pharmaceutically acceptable derivative" in present context includes pharmaceutically acceptable salts, which indicate a salt which is not harmful to the patient. Such salts include pharmaceutically acceptable basic or acid addition salts as well as pharmaceutically acceptable metal salts, ammonium salts and alkylated ammonium salts. A pharmaceutically acceptable derivative further includes esters and prodrugs, or other precursors of a compound which may be biologically metabolized into the active compound, or crystal forms of a compound.

The terms "serotonin," "5-hydroxytryptamine" and "5-HT" refers to a phenolic amine neurotransmitter produced from tryptophan by hydroxylation and decarboxylation in serotonergic neurons of the central nervous system and enterochromaffin cells of the gastrointestinal tract. Serotonin is a precursor of melatonin.

The term "therapeutically effective amount" of a compound as used herein refers to an amount sufficient to cure, alleviate, prevent, reduce the risk of, or partially arrest the clinical manifestations of a given disease or disorder and its complications.

The terms "treatment" and "treating" as used herein refer to the management and care of a patient for the purpose of combating a condition, disease or disorder. The term is intended to include the full spectrum of treatments for a given condition from which the patient is suffering, such as administration of the active compound for the purpose of: alleviating or relieving symptoms or complications; delaying the progression of the condition, disease or disorder; curing or eliminating the condition, disease or disorder; and/or preventing the condition, disease or disorder, wherein "preventing" or "prevention" is to be understood to refer to the management and care of a patient for the purpose of hindering the development of the condition, disease or disorder, and includes the administration of the active compounds to prevent or reduce the risk of the onset of symptoms or complications. The patient to be treated is preferably a mammal, in particular a human being.

A "triptan" in the present context is a compound part of a family of tryptamine-based drugs used as abortive medication in the treatment of migraines and cluster headaches. The triptans are agonists of several of the serotonin receptors (such as two or more), with varying potency for the different 5-HT1 receptor subtypes, primarily 5-HT1B, 5-HT1D, 5-HT1E and/or 5-HT1F receptors.

"Partial agonists" in the present context are compounds able to bind and activate a given receptor, but having only partial efficacy at the receptor relative to a "full agonist". Partial agonists can act as antagonists when competing with a full agonist for receptor occupancy and producing a net decrease in the receptor activation compared to the effects or activation observed with the full agonist alone.

The terms "extended release" (ER), "sustained release" (SR) and "controlled release" (CR) have the same meaning and are used interchangeably herein.

DESCRIPTION OF DRAWINGS

FIG. 3 and Example III); and B) simulated release of active ingredients in a combination formulation with the release properties as described in claim 1, at one day dosing regimen, thus obtaining the beneficial effects of sequential administration of zolmitriptan and buspirone shown by injections in an orally available combination formulation. A steady-state level of zolmitriptan is achieved, with peak bolus doses of buspirone.

DETAILED DESCRIPTION OF THE INVENTION

Figure 1:
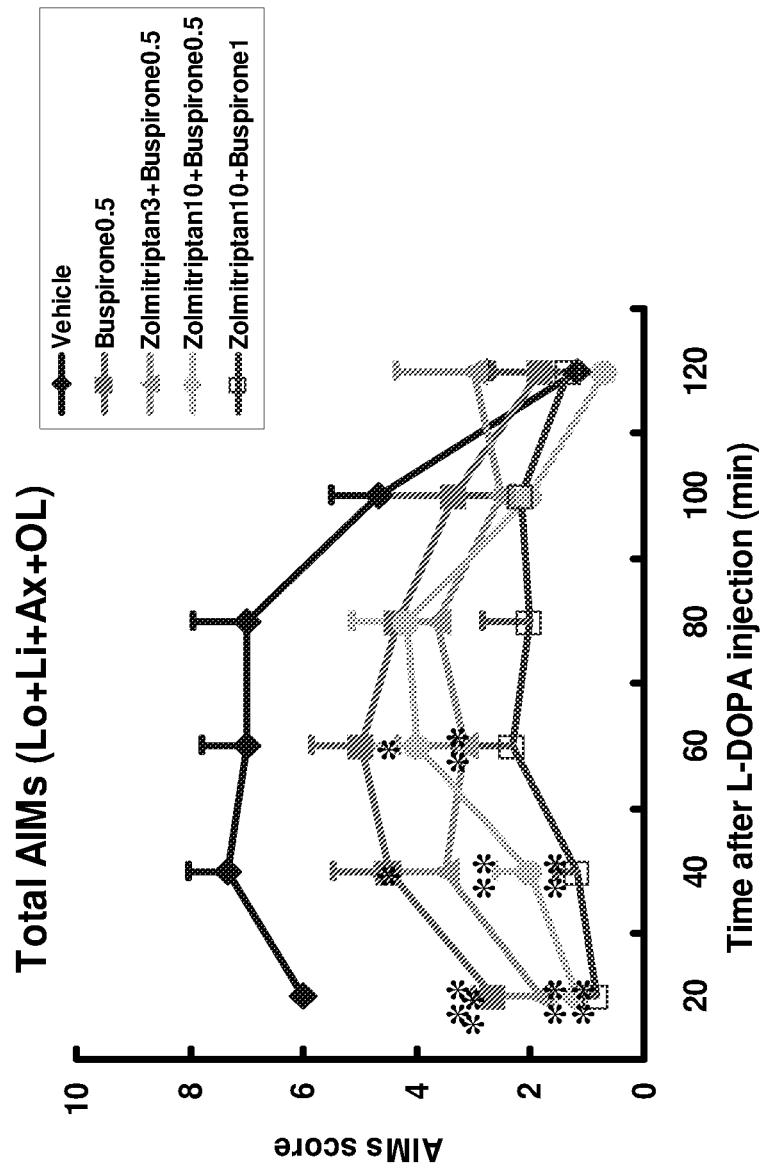
FIG. 1: Effect of combination of buspirone and zolmitriptan on L-DOPA induced abnormal involuntary movements (AIMs) in rats. Asterics (**) denote effects of P<0.01 compared with vehicle. Zolmitriptan was given 35 minutes before L-DOPA while buspirone was given 30 minutes before L-DOPA. Diamonds denote rats administered vehicle only, filled square denote rats administered 0.5 mg/kg buspirone, triangles denote rats administered 3 mg/kg zolmitriptan in combination with 0.5 mg/kg buspirone, filled circles denote rats administered 10 mg/kg zolmitriptan in combination with 0.5 mg/kg buspirone and open squares denote rats administered 10 mg/kg zolmitriptan in combination with 1 mg/kg buspirone. The curves show different treatments: buspirone (0.5 mg/kg); buspirone (0.5 mg/kg)+zolmitriptan (3 mg/kg); buspirone (0.5 mg/kg)+zolmitriptan (10 mg/kg) and buspirone (1 mg/kg)+zolmitriptan (10 mg/kg). Detailed in Example I.

The present invention relates to the use of combinations of serotonin receptor agonists (5-HT1A agonist and serotonin 5-HT1D, 5-HT1B, 5-HT1F agonists; ie. "triptans") for treatment of movement disorders, wherein the agonist of serotonin receptors selected from the group of 5-HT1B, 5-HT1D, and 5-HT1F or "triptan" and the serotonin 5-HT1A receptor agonist are released or administered in a special sequence that will optimize the effects of the individual components in such a way that optimal additive or synergistic activity is obtained. This will further improve efficacy or reduce adverse effects (i.e. increase therapeutic index). By administering the "triptan" in a way that will allow the "triptan" to affect its molecular target in the relevant brain region during and/or before and/or after the 5-HT1A receptor agonist affect its molecular target beneficial effects will be achieved. An extended release procedure will allow the "triptan" to affect the molecular target in the relevant brain region before and/or during the time where the 5-HT1A agonist affects its molecular target. By allowing a sequential modulation of the relevant brain region it will be possible to achieve an improved efficacy and reduced adverse effects by using lower doses of the two compounds.

In the present context, for the purposes of the present invention, to achieve the effect of the administration of the agonist of two or more of 5-HT1B, 5-HT1D and 5-HT1F receptors before and/or during release or administration of the 5-HT1A receptor agonist, the agonist of two or more of 5-HT1B, 5-HT1D and 5-HT1F receptors is released by extended release during immediate release of the 5-HT1A agonist.

Provided herein is a special pharmaceutical formulation that is designed to obtain the beneficial synergistic effects of combining an agonist of two or more of the 5-HT1B, D and F receptors, exemplified by zolmitriptan, with a 5-HT1A agonist, exemplified by buspirone; and moreover surprisingly also achieving the additional beneficial effect of sequential administration of the two active components, thus increasing the therapeutic index by improving efficacy and reducing the risk of adverse effects.

The movement disorders which are intended to be treated with the advantageous combination of drugs as identified are mainly chronic conditions which require chronic management and thus often life-long medical treatment. Thus, in order to ensure optimal compliance of the patient it is highly advantageous to develop an orally available pharmaceutical formulation, such as a solid dosage form or tablet, which will allow for ease of administration—by avoiding the need for injections overall, and specifically avoiding the need for injections (or ingestion of tablets) separated in time (such as zolmitriptan 2-5 hours before buspirone, and both administered daily). Also, a peak dose of zolmitriptan is avoided by this special formulation thus eliminating a potential safety concern, and the peak dose of buspirone is kept relatively low by being potentiated by zolmitriptan, thus reducing the risk of developing the serotonin syndrome.

The serotonin syndrome is caused by increased activation of the 5-HT1A and 5-HT2A receptors. Serotonin syndrome, by definition, is a group of symptoms presenting as mental changes, autonomic nervous system malfunction, and neuromuscular complaints. Patients may present with confusion, agitation, diarrhoea, sweating, shivering, hypertension, fever, increased white blood cell count, incoordination, marked increase in reflexes, muscle jerks, tremor, extreme stiffness, seizures and even coma. The severity of changes ranges from mild to fatal.

Pharmaceutical Formulation

The pharmaceutical formulation as disclosed herein is formulated for enteral administration, more specifically oral administration.

It is an aspect of the present invention to provide a pharmaceutical formulation comprising
   a. a matrix constituent comprising an active pharmaceutical ingredient being an agonist of two or more of the 5-HT1B, 5-HT1D and 5-HT1F receptors, said matrix constituent providing for extended release of said active pharmaceutical ingredient, and
   b. a constituent comprising an active pharmaceutical ingredient being an agonist of the 5-HT1A receptor, said constituent providing for immediate release of said active pharmaceutical ingredient.

The present pharmaceutical formulation thus comprises two constituents; constituents a. and b., each comprising an active pharmaceutical ingredient; wherein constituent a. comprises i) an agonist of two or more the 5-HT1B, 5-HT1D and 5-HT1F receptors, and constituent b. comprises ii) an agonist of the 5-HT1A receptor.

The pharmaceutical formulation according to the present invention is thus designed to release the two active ingredients differently; matrix constituent a. is a matrix providing for extended release of component i) an agonist of two or more of the 5-HT1B, 5-HT1D and 5-HT1F receptors, and constituent b. provides for immediate release of an agonist of component ii) the 5-HT1A receptor (being a matrix or a coating).

Time—or controlled release technology (extended or sustained release) is a mechanism used in pill tablets or capsules to dissolve slowly and release a drug over time. The advantages of extended-release tablets or capsules are that they may be taken less frequently than immediate-release formulations, and that they keep steadier levels of the drug in the bloodstream.

Controlled-release drugs may be formulated so that the active ingredient is embedded in a matrix of insoluble substance(s) such that the dissolving drug must find its way out through the holes in the matrix. Some drugs are enclosed in polymer-based tablets with a laser-drilled hole on one side and a porous membrane on the other side. Stomach acids push through the porous membrane, thereby pushing the drug out through the laser-drilled hole. In time, the entire drug dose releases into the system while the polymer container remains intact, to be excreted later through normal digestion. In some formulations, the drug dissolves into the matrix, and the matrix physically swells to form a gel, allowing the drug to exit through the gel's outer surface. Micro-encapsulation also produces complex dissolution profiles; through coating an active pharmaceutical ingredient around an inert core, and layering it with insoluble substances to form a microsphere a more consistent and replicable dissolution rate is obtained—in a convenient format that may be mixed with other instant release pharmaceutical ingredients, e.g. into any two piece gelatin capsule.

Dosage forms are a mixture of active drug components and nondrug components. The pharmaceutical formulation according to the present invention may be a dosage form, such as an oral dosage form. In a particular embodiment, said dosage form is a solid dosage form, such as a tablet.

Solid dosage forms (or solid form preparations) include powders, tablets, pills, capsules, cachets, suppositories, and dispersible granules.

According to the present invention, in the same solid dosage form two active ingredients may in one embodiment be combined so as to provide controlled release of one active ingredient and immediate release of another active ingredient. A tablet is a pharmaceutical dosage form comprising a mixture of active substances and excipients, pressed or compacted into a solid dose. Tablets are simple and convenient to use. They provide an accurately measured dosage of the active ingredient(s) in a convenient portable package. Manufacturing processes and techniques can provide tablets special properties, for example, extended release or fast dissolving formulations.

In one embodiment, the two constituents a. and b. each comprising an active ingredient (i) and ii) respectively) according to the present invention are provided in a solid dosage form or a tablet, wherein said active ingredients are provided in separate compartments or layers within the tablet. Said separate compartments or layers may be any design conceivable to the skilled person, such as an inner layer of constituent a. or b. with an outer layer of constituent b. or a.; or a bilayer of any conceivable form, such as a layer of constituent a. or b. with another layer of constituent b. or a.

In one embodiment, said pharmaceutical composition is a bi-layered solid dosage form or a bi-layered tablet.

It follows that in one embodiment, there is provided a solid dosage form that comprises
   a. a matrix constituent providing for extended release of an agonist of two or more of the 5-HT1B, 5-HT1D and 5-HT1F receptors, and
   b. a constituent providing for immediate release of an agonist of the 5-HT1A receptor, wherein said dosage form comprises matrix constituent a. and constituent b. in separate compartments or layers.

In a particular embodiment the pharmaceutical formulation according to the present invention comprises
  a. an inner core matrix providing for extended release of an agonist of two or more of the 5-HT1B, 5-HT1D and 5-HT1F receptors, and
  b. an outer coating providing for immediate release of an agonist of the 5-HT1A receptor.

In one embodiment, each of constituents a. and b. of the pharmaceutical formulation according to the present invention are provided together in a capsule. Said capsule may comprises constituents a. and b. as separate granules or pellets.

Thus, the invention provides for a formulation (such as a tablet) that is designed to slowly release the compound being an agonist of two or more of the 5-HT1B, 5-HT1D and 5-HT1F receptors (or triptan) by an extended (or delayed, sustained) release procedure, and release the 5-HT1A receptor agonist by an immediate release procedure.

The inner core matrix and the outer coating in one embodiment further comprises one or more excipients, as detailed herein elsewhere.

In a preferred embodiment, component i) is a triptan, and component ii) is a 5-HT1A agonist. In a preferred embodiment, component i) is a triptan selected from the group consisting of zolmitriptan, rizatriptan, sumatriptan, naratriptan, almotriptan, frovatriptan, eletriptan, avitriptan and imotriptan, and component ii) is a 5-HT1A agonist selected from the group consisting of buspirone, tandospirone, gepirone, alnespirone, binospirone, ipsapirone, perospirone, befiradol, repinotan piclozotan, osemozotan, flesinoxan, flibanserin and sarizotan. In a particular embodiment, component i) is zolmitriptan and component ii) is buspirone.

Matrix constituent a. comprising component i) is formulated to release the active ingredient by a controlled release rate over time (extended release), thus achieving a slow and constant release of component i) thereby achieving a steady-state situation with a constant plasma concentration of component i). The extended release formulation will provide a steady state plasma concentration of the compound, and a more flat plasma concentration curve avoiding high peak plasma concentrations, that provides for a prolonged exposure as compared to immediate release.

Constituent b. comprising component ii) is formulated to release the active ingredient by an immediate release procedure, thus achieving a peak plasma concentration of component ii). The immediate release procedure of the 5-HT1A agonist can mimic a bolus administration i.e. the administration of a substance in the form of a single, larger dose. This will provide a peak dose of the 5-HT1A agonist.

Constituent b. may in one embodiment be formulated as an outer coating situated on or outside the inner core matrix, substantially covering the inner core matrix.

Constituents a. and b. may in one embodiment each be formulated as a separate layer in a bi-layered tablet.

The present design of pharmaceutical formulation, dosage form or tablet provides for component i) being an agonist of two or more the 5-HT1B, 5-HT1D and 5-HT1F receptors to be present at low continuous plasma levels thus constantly affecting its molecular targets in the relevant brain region, thus component i) being present and ready to potentiate the effects of component ii) a 5-HT1A agonist when the latter is released to achieve its peak plasma levels. Thus the therapeutic ratio is optimised by using lower doses of each of the two compounds (synergy) and avoiding a peak exposure of component i).

Figure 4:
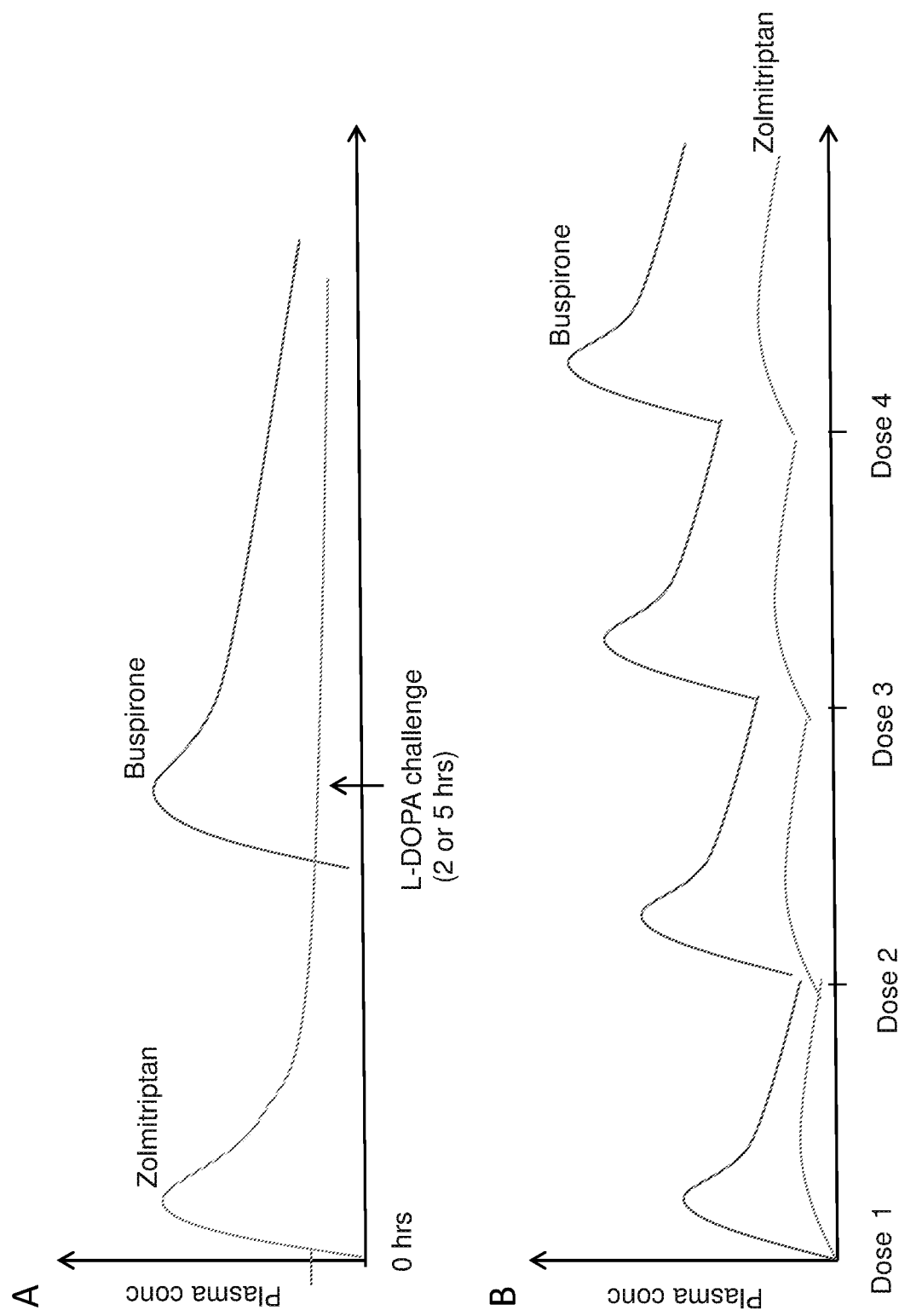
FIG. 4: Comparison of generalized results for A) sequential administration of zolmitriptan and buspirone by injection on plasma concentration levels of zolmitriptan and buspirone in an animal model of LID (6-OHDA, described in Examples I-III); zolmitriptan is administered 2 or 5 hours before L-DOPA challenge and buspirone administered shortly before L-DOPA challenge (see e.g.

The first administration of the tablet according to the present invention (dose 1' in FIG. 4B) will provide a peak plasma concentration of component ii) a 5-HT1A agonist while the plasma levels of component i) an agonist of two or more the 5-HT1B, 5-HT1D and 5-HT1F receptors are more slowly rising to a low steady state level in the plasma. Thus providing multiple dosages will achieve an optimal synergistic effect of the two active ingredients by 'mimicking' sequential administration of components i) and ii).

Thus, component i) an agonist of two or more the 5-HT1B, 5-HT1D and 5-HT1F receptors is released by extended release during and/or after immediate release of component ii) the 5-HT1A agonist.

The term "immediate-release" refers to a pharmaceutical formulation (such as tablets or capsules) capable of releasing the active ingredient within a short period of time, typically within less than 30 minutes.

The term "extended-release" refers to tablets or capsules releasing the active ingredient at a sustained and controlled release rate over a period of time. Typically extended-release tablets and capsules release all or most of their active ingredient within a time period of 4 hours, such as 8 hours, for example 12 hours, such as 16 hours, for example 24 hours.

Active Ingredients

The present pharmaceutical formulation comprises two active ingredients i) an agonist of two or more the 5-HT1B, 5-HT1D and 5-HT1F receptors, and ii) a 5-HT1A agonist.

Component i)

In one embodiment, the component i) agonist of two or more the 5-HT1B, 5-HT1D and 5-HT1F receptors is an agonist of two or three serotonin receptors selected from the group consisting of 5-HT1B, 5-HT1D, and 5-HT1F receptors. Thus component i) may be a combined agonist of the 5-HT1B receptor and 5-HT1D receptor, or a combined agonist of the 5-HT1B receptor and 5-HT1F receptor, or a combined agonist of the 5-HT1D receptor and 5-HT1F receptor, or a combined agonist of the 5-HT1B receptor, the 5-HT1D receptor and the 5-HT1F receptor. In one embodiment, said component i) is also an agonist of the 5-HT1A receptor (full or partial).

An agonist identified as component i) may have different affinity and/or receptor activation efficacy for each of the two or more serotonin receptors, wherein affinity refers to the number and size of intermolecular forces between a ligand and its receptor, and residence time of a ligand at its receptor binding site, and receptor activation efficacy refers to the ability of the compound to produce a biological response upon binding to the target receptor and the quantitative magnitude of this response. Such differences in affinity and receptor activation efficacy can be determined by receptor binding/activation studies which are conventional in the art, for instance by generating $EC_{50}$ and Emax values for stimulation of $[^{35}S]$-GTPγS binding in cells expressing one or several types of 5-HT1 receptors as mentioned herein, or on tissues expressing the different types of 5-HT receptors. High affinity means that a lower concentration of a compound is needed to obtain a binding of 50% of the receptors compared to compounds which have lower affinity; high receptor activation efficacy means that a lower concentration of the compound is needed to obtain a 50% receptor activation response (low $EC_{50}$ value), compared to compounds which have lower affinity and/or receptor activity efficacy (higher $EC_{50}$ value). The receptor activation potency of compounds which are 5-HT1 receptor agonists of the present invention can also be measured in $p(A_{50})$ values which is a conventional method for determining the receptor activation efficacy of an agonist.

In one embodiment, the combined agonist of two or three of the 5-HT1B, the 5-HT1D and the 5-HT1F receptors has higher affinity and/or receptor activation efficacy for the 5-HT1D receptor than for the 5-HT1B receptor, or has higher affinity and/or receptor activation efficacy for the 5-HT1D receptor than for the 5-HT1B and 5-HT1F receptors.

Certain mixed 5-HT1B/5-HT1D receptor agonists have been developed, and a subgroup of 5-HT1B/5-HT1D receptor agonists are collectively called "the triptans". The triptans have been developed as medication for treatment of migraine and have been used for therapy for more than a decade. In addition to their effects on 5-HT1B and 5-HT1D receptors, some "triptans" bind to and activate 5-HT1F receptors and other 5-HT receptors.

Component i) agonist of two or more the 5-HT1B, 5-HT1D and 5-HT1F receptors may be selected from the group consisting of zolmitriptan ((S)-4-({3-[2-(dimethylamino)ethyl]-1H-indol-5-yl}methyl)-1,3-oxazolidin-2-one), rizatripan (N,N-dimethyl-2-[5-(1H-1,2,4-triazol-1-ylmethyl)-1H-indol-3-yl]ethanamine), sumatriptan (1-[3-(2-dimethylaminoethyl)-1H-indol-5-yl]-N-methyl-methanesulfonamide), naratripan (N-methyl-2-[3-(1-methylpiperidin-4-yl)-1H-indol-5-yl]ethanesulfonamide), almotriptan (N,N-dimethyl-2-[5-(pyrrolidin-1-ylsulfonylmethyl)-1H-indol-3-yl]-ethanamine), frovatriptan ((+)-(R)-3-methylamino-6-carboxamido-1,2,3,4-tetrahydrocarbazole) and eletriptan ((R)-3-[(-1-methylpyrrolidin-2yl)methyl]-5-(2-phenylsulfonylethyl)-1H-indole), or a pharmaceutically acceptable derivative thereof.

Thus, in a preferred embodiment, the component i) agonist of two or more the 5-HT1B, 5-HT1D and 5-HT1F receptors is a 'triptan'. In one embodiment, said triptan is selected from the group consisting of zolmitriptan, rizatriptan, sumatriptan, naratriptan, almotriptan, frovatriptan, avatriptan, imotriptan and eletriptan, and pharmaceutically acceptable derivatives thereof.

In a particular embodiment, said triptan is zolmitriptan, rizatripan, frovatriptan, eletriptan or naratriptan.

Zolmitriptan, rizatriptan, naratriptan and eletriptan are full agonists of 5-HT1D, B and A, and partial agonists of 5-HT1B.

Component ii)

Component ii) a 5-HT1A agonist may be selected from the group consisting of buspirone (8-[4-(4-pyrimidin-2-ylpiperazin-1-yl)butyl]-8-azaspiro[4.5]decane-7,9-dione), tandospirone ((1R,2R,6S,7S)-4-{4-[4-(pyrimidin-2yl)piperazin-1-yl]butyl}-4-azatricyclo[5.2.1.02,6]decane-3,5-dione), gepirone (4,4-dimethyl-1-[4-(4-pyrimidin-2-ylpiperazin-1-yl)butyl]piperidine-2,6-dione), alnespirone ((+)-4-dihydro-2H-chromen-3-yl]-propylamino]butyl]-8-azaspiro[4.5]decane-7,9-dione), binospirone (8-[2-(2,3-dihydro-1,4-benzodioxin-2-ylmethylamino)ethyl]-8-azaspiro[4.5]decane-7,9-dione), ipsapirone (9,9-dioxo-8-[4-(4-pyrimidin-2-ylpiperazin-1-yl)butyl]-9λ6-thia-8-azabicyclo[4.3.0]nona-1,3,5-trien-7-one), perospirone (3aR, 7aS)-2-{4-[4-(1,2-benzisothiazol-3-yl)piperazin-1-yl]butyl}hexahydro-1H-isoindole-1,3(2H)-dione, befiradol (F-13,640) (3-chloro-4-fluorophenyl-[4-fluoro-4-([(5-methylpyridin-2-yl)methylamino]methyl)piperidin-1-yl]methanone, repinotan ((R)-(−)-2-[4-[(chroman-2-ylmethyl)-amino]-butyl]-1,1-dioxo-benzo[d]isothiazolone), piclozotan (3-chloro-4-[4-[4-(2-pyridinyl)-1,2,3,6-tetrahydropyridin-1-yl]butyl]-1,4-benzoxazepin-5(4H)-one), osemozotan (5-(3-[((2S)-1,4-benzodioxan-2-ylmethyl)amino]propoxy)-1,3-benzodioxole), flesinoxan (4-fluoro-N-[2-[4-[(3S)-3-(hydroxymethyl)-2,3-dihydro-1,4-benzodioxin-8-yl]piperazin-1-yl]ethyl]benzamide), flibanserin (1-(2-{4-[3-(trifluoromethyl)phenyl]piperazin-1-yl}ethyl)-1,3-dihydro-2H-benzimidazol-2-one), and sarizotan (EMD-128,130) (1-[(2R)-3,4-dihydro-2H-chromen-2-yl]-N-([5-(4-fluorophenyl)pyridin-3-yl]methyl)methanamine), or a pharmaceutically acceptable derivative thereof.

Thus, in a preferred embodiment, the component ii) a 5-HT1A agonist is selected from the group consisting of buspirone, tandospirone, gepirone, alnespirone, binospirone, ipsapirone, perospirone, befiradol, repinotan piclozotan, osemozotan, flesinoxan, flibanserin and sarizotan, and pharmaceutically acceptable derivatives thereof.

In a particular embodiment said 5-HT1A agonist is buspirone, tandospirone or gepirone. In another particular embodiment said 5-HT1A agonist is buspirone or tandospirone. In yet another particular embodiment said 5-HT1A agonist is buspirone.

In a preferred embodiment, the agonist of two or more the 5-HT1B, 5-HT1D and 5-HT1F receptors is zolmitriptan, and the 5-HT1A agonist is buspirone.

Administration and Dosage

The pharmaceutical formulation of the present invention induces combined and synergistic effects, which enable for a lowered dosage of 5-HT1 agonists in the treatment of movement disorders, resulting in a reduced risk of adverse effects of high-dose treatment with 5-HT1 agonists.

According to the present invention, 5-HT1 agonists are administered to individuals in need of treatment in pharmaceutically effective doses. A therapeutically effective amount of a compound according to the present invention is an amount sufficient to cure, prevent, reduce the risk of, alleviate or partially arrest the clinical manifestations of a given disease or movement disorder and its complications. The amount that is effective for a particular therapeutic purpose will depend on the severity and the sort of the movement disorder as well as on the weight and general state of the subject.

The special formulation tablet according to the present invention may be administered one or several times per day, such as from 1 to 8 times per day, such as from 1 to 6 times per day, such as from 1 to 5 times per day, such as from 1 to 4 times per day, such as from 1 to 3 times per day, such as from 1 to 2 times per day, such as from 2 to 4 times per day, such as from 2 to 3 times per day. In a particular embodiment, the formulation or tablet is administered once a day, such as twice per day, for example 3 times per day, such as 4 times per day, for example 5 times per day, such as 6 times per day.

Administration may occur for a limited time, such as from 1 or 2 days to 7 days, for example 7 days to 14 days, such as from 14 days to a month, for example from a month to several months (2, 3, 4, 5, 6, 7, 8, 9, 10, 11, 12 months); or administration may be chronic, the treatment may be chronic from the onset of diagnosis, such as throughout the lifetime of the individual or as long as the individual will benefit therefrom i.e. when a movement disorder is present or while having an increased risk of developing a movement disorder, such as during treatment with L-DOPA or other medications such as antipsychotics, antidepressants, anti-emetic drugs or during withdrawal of certain medications causing a movement disorder.

In one embodiment, the pharmaceutical formulation is to be administered as long as a movement disorder is present or as long as an increased risk of developing a movement disorder is present.

The administration of the pharmaceutical formulation according to the present invention may be administered to an individual at various time points of treatment. The treatment may be done over one continued period, or in intervals with periods in between wherein the administration is stopped, decreased or altered. Such treatment periods or non-treatment periods may vary in length, and can be from 1 day to 60 days, such as 1 to 3 days, 3 to 6 days, 6 to 8 days, 8 to 14 days, 14 to 21 days, 21 to 30 days, 30 to 42 days, 42 to 49 days or 49 to 60 days.

The concentration of each of the active ingredients in the present pharmaceutical formulation namely component i) an agonist of two or more the 5-HT1B, 5-HT1D and 5-HT1F receptors, and component ii) a 5-HT1A agonist are optimized to achieve an appropriate dosage of each drug.

In the pharmaceutical composition according to the present invention, the composition will in one embodiment comprise component i) an agonist of two or more the 5-HT1B, 5-HT1D and 5-HT1F receptors in an amount of from 0.01 to 100 mg per dosage; such as about 0.01, 0.05, 0.1, 0.5, 1, 2, 3, 4, 5, 6, 7, 8, 9, 10, 15, 20, 25, 50 or 100 mg of active ingredient per dosage. Likewise, said pharmaceutical composition will invariably further comprise component ii) a 5-HT1A agonist, in one embodiment in an amount of from 0.01 to 100 mg per dosage; such as about 0.01, 0.05, 0.5, 1, 2, 3, 4, 5, 6, 7, 8, 9, 10, 15, 20, 25, 50 or 100 mg of active ingredient per dosage. Dosage may refer to dosage form, tablet or capsule.

In a further embodiment, component i) an agonist of two or more the 5-HT1B, 5-HT1D and 5-HT1F receptors and component ii) a 5-HT1A agonist are each present in the formulation in an amount of from 0.01 to 0.05 mg, such as from 0.05 to 0.1 mg, for example 0.1 to 0.5 mg, such as from 0.5 to 1 mg, for example 1 to 2 mg, such as 2 to 3 mg, for example 3 to 4 mg, such as 4 to 5 mg, for example 5 to 7.5 mg, such as 7.5 to 10 mg, for example 10 to 15 mg, such as 15 to 20 mg, for example 20 to 30 mg, such as 30 to 40 mg of active ingredient per dosage.

In a particular embodiment, the amount of component i) in the pharmaceutical composition is about 1 mg and the amount of component ii) in the pharmaceutical composition is about 10 mg, wherein component i) is a triptan such as zolmitriptan, and component ii) is a 5-HT1A agonist such as buspirone.

The dosage desired for each of components i) and ii) are within the range of from 0.001 to 100 mg/kg bodyweight, such as 0.001 to 0.005 mg/kg, for example 0.005 to 0.01 mg/kg, such as 0.01 to 0.05 mg/kg, for example 0.05 to 0.1 mg/kg, such as 0.1 to 0.5 mg/kg, for example 0.5 to 1.0 mg/kg, such as 1 to 2 mg/kg, for example 2 to 5 mg/kg, such as 5 to 10 mg/kg, for example 10 to 15 mg/kg, such as 15 to 20 mg/kg, for example 20 to 30 mg/kg, such as 30 to 40 mg/kg, for example 50 to 75 mg/kg, such as 75 to 100 mg/kg bodyweight.

In a particular embodiment the dosage of component i) an agonist of two or more the 5-HT1B, 5-HT1D and 5-HT1F receptors is between 0.001 to 10 mg/kg bodyweight, such as 0.001 to 5 mg/kg bodyweight, such as 0.01 to 1 mg/kg bodyweight.

In a particular embodiment the dosage of component ii) a 5-HT1A agonist is between 0.01 to 10 mg/kg bodyweight, such as 0.01 to 5 mg/kg bodyweight, such as 0.1 to 1 mg/kg bodyweight.

Pharmaceutical Formulation—Excipients

The pharmaceutical formulation or fixed-dose combination product according to the present invention will comprise the active pharmaceutical ingredients (API) as detailed herein elsewhere, as well as one or more excipients.

An excipient is generally a pharmacologically inactive substance formulated with the active ingredient (API) of a medication. Excipients are commonly used to bulk up formulations that contain potent active ingredients (thus often referred to as "bulking agents," "fillers," or "diluents"), to allow convenient and accurate dispensation of a drug substance when producing a dosage form.

In one embodiment, the pharmaceutical formulation according to the present invention comprises one or more excipients. Said one or more excipients may act as a solid carrier, diluent, flavouring agent, solubilizer, lubricant, glidants, suspending agent, binder, filler, preservative, antiadherents, wetting agent, tablet disintegrating agent, sorbent, and/or an encapsulating/coating material.

The present pharmaceutical formulation comprises at least one excipient in order to obtain a suitable formulation such as a dosage form for oral administration with the ER (extended release) and IR (immediate release) characteristics, respectively, as desired.

In one embodiment the pharmaceutical formulation according to the invention comprises at least one type of hydroxypropylmethylcellulose (HPMC) also known as hypromellose. HPMC is used as an excipient in oral tablet and capsule formulations, where, depending on the grade, it functions as a controlled release agent or release-controlling excipient to delay the release of a medicinal compound into the digestive tract. It is also used as a binder and as a component of tablet coatings.

As detailed elsewhere, the pharmaceutical formulation or tablet according to the present invention comprises matrix constituent a. comprising an agonist of two or more the 5-HT1B, 5-HT1D and 5-HT1F receptors, such as a triptan, exemplified by zolmitriptan, and constituent b. comprising a 5-HT1A agonist, exemplified by buspirone.

Matrix constituent a. is formulated to release the active ingredient (component i)) by an controlled release procedure or rate, namely by extended release, while constituent b. is formulated for immediate release of the active ingredient (component ii)).

In one embodiment, matrix constituent a. is an inner core matrix, and constituent b. is an outer coating.

In one embodiment, matrix constituent a. is a component or matrix in a bi-layered dosage form or tablet, and constituent b. is another component or matrix in the same bi-layered dosage form or tablet.

Matrix Constituent a.

In one embodiment, matrix constituent a. comprises an agonist of two or more the 5-HT1B, 5-HT1D and 5-HT1F receptors and one or more release-controlling excipients, and optionally one or more further excipients such as fillers, binders and lubricants.

Release controlling excipients may be any release controlling excipient known to the skilled person. Release controlling excipients (or agents) may in one embodiment be an excipient selected from the group consisting of hydroxypropylmethylcellulose (HPMC), methylcellulose, hydroxypropyl cellulose, hypromellose acetate succinate, hypromellose phthalate, cellulose acetate, glycerin monostearate, glyceryl monooleate, glyceryl palmitate, glyceryl behenate, hydrogenated vegetable oil, guar gum, polyvinyl alcohol, alginates, xanthan gum, carnauba wax, yellow wax, white wax, zein, carregeenan, carbomers and agar.

In one embodiment, matrix constituent a. further comprises a filler, such as a filler selected from the group consisting of calcium carbonate, calcium phosphates, calcium sulfate, cellulose, cellulose acetate, compressible sugar, dextrate, dextrin, dextrose, ethylcellulose, fructose, isomalt, lactitol, lactose, mannitol, magnesium carbonate, magnesium oxide, maltodextrin, microcrystalline cellulose (MCC), polydextrose, sodium alginate, sorbitol, talc and xylitol.

In one embodiment, matrix constituent a. further comprises a binder, such as a binder selected from the group consisting of acacia, alginic acid, carbomers, carboxymethylcellulose sodium, carrageenan, cellulose acetate phthalate, chitosan, copovidone, dextrate, dextrin, dextrose, ethylcellulose, gelatin, guar gum, hydroyethyl cellulose, hydroxyethylmethyl cellulose, hydroxypropyl cellulose, hydroxypropyl starch, hypromellose, methylcellulose, poloxamer, polydextrose, polyethylene oxide, povidone, sodium alginate, sucrose, starch, pregelatinized starch and maltodextrin.

In one embodiment, matrix constituent a. further comprises a lubricant, such as a lubricant selected from the group consisting of calcium stearate, glycerin monostearate, glyceryl behenate, glyceryl palmitostearate, hydrogenated castor oil, hydrogenated vegetable oil, magnesium lauryl sulfate, magnesium stearate, medium chain triglyceride, palmitic acid, polyethylene glycol, sodium lauryl sulfate, stearic acid, talc, silica, stearic acid and zinc stearate.

Any other excipients suitable for the purpose of the present invention and known to the skilled person are considered encompassed by the present invention.

Different grades of HPMC have different characteristics with respect to e.g. viscosity. Thus, different HPMCs will have different impacts on the release rates of the embedded API. Also, the amount of HPMC in the formulation, the hardness or degree of compression of the formulation into a tablet, as well as any potential coatings, will potentially impact the release rates of the API. The release rates may be determined by evaluating the dissolution profiles of the produced granules or batches. In vitro drug dissolution data generated from dissolution testing experiments can be related to in vivo pharmacokinetic data by means of in vitro-in vivo correlations (IVIVC). Several dissolution apparatuses exist.

In one embodiment, matrix constituent a. comprises one or more excipients. In one embodiment, matrix constituent a. comprises one or both of the excipients hydroxypropylmethylcellulose (HPMC) and microcrystalline cellulose (MCC).

In a particular embodiment, matrix constituent a. comprises one or more (such as 2 or 3) types of HPMC. In one embodiment said HPMC is selected from Methocel K100 and Methocel E4M, preferably comprising Methocel E4M (Methocel E4M Premium). Matrix constituent a. may thus comprise Methocel K100 and/or Methocel E4M.

The release-controlling excipient such as HPMC of matrix constituent a. is in one embodiment present in an amount of from 20-50%, such as 20-25%, for example 25-30%, such as 30-35%, for example 35-40%, such as 40-45%, for example 45-50% (with respect to the total contents of matrix constituent a. only—not including the coating). In a particular embodiment, the release-controlling excipient such as HPMC is present in an amount of from 20-40%, for example 25-35%, such as about 30%.

In a particular embodiment, the matrix comprising constituent a. comprises two release-controlling excipients. In one particular embodiment, HPMC is mixed with microcrystalline cellulose (MCC) to achieve a MCC/HPMC matrix. The MCC is in a particular embodiment Avicel PH 101. The second excipient, such as MCC, is in one embodiment present in an amount of from 50 to 80%, such as 50 to 60%, for example 60-65%, such as 65-70%, for example 70-80% (with respect to the total contents of matrix constituent a. only—not including the coating). In a particular embodiment, the MCC is present in an amount of about 65%, such as 65% minus the percentage part made up of the API such as zolmitriptan.

Furthermore, matrix constituent a. in one embodiment comprises talc; a mineral composed of hydrated magnesium silicate with the chemical formula $H_2Mg_3(SiO_3)_4$ or $Mg_3Si_4O_{10}(OH)_2$. The amount of talc in matrix constituent a. may be from 1 to 10%, such as 1-2%, for example 2-3%, such as 3-4%, for example 4-5%, such as 5-6%, for example 6-7%, such as 7-8%, for example 8-9%, such as 9-10% (with respect to the total contents of the inner core matrix only—not including the coating). Preferably, talc constitutes about 5% of matrix constituent a.

In one embodiment matrix constituent a. is compressed to form a tablet, with a hardness of from 40 to 80N, such as from 40-45N, for example 45-50N, such as from 50-55N, for example 55-60N, such as from 60-65N, for example 65-70N, such as from 70-75N, for example 75-80N. In a preferred embodiment, the tablet hardness is about 60N.

For the purposes of the present invention matrix constituent a. components are formulated in order to optimize drug release rates (not too slow and not too fast) and achieving a maximum release of API of more than 70%, preferably more than 80% or more than 85%, such as between 80-85%, for example 85-90%, such as about 90%.

Preferably, in one embodiment said inner core matrix provides for at least between 80-90% release of the agonist of two or more of the 5-HT1B, 5-HT1D and 5-HT1F receptors after 12 hours.

Constituent b.

In one embodiment, constituent b. comprises a 5-HT1A agonist and one or more excipients, such as one or more film-forming excipients, binders, fillers, disintegrants or lubricants.

Film forming excipients may be any film-forming excipient known to the skilled person. Film forming excipients (or agents) may in one embodiment be an excipient selected from the group consisting of hydroxypropylmethylcellulose (HPMC), methylcellulose, hydroxyethyl cellulose, hydroxypropyl cellulose, hypromellose acetate succinate, hypromellose phthalate, chitosan, copovidone, ethylcellulose, gelatin, cellulose acetate, polymethacrylates, polyvinyl alcohol and alginates.

In one embodiment, matrix constituent b. further comprises a filler, such as a filler selected from the group consisting of calcium carbonate, calcium phosphates, calcium sulfate, cellulose, cellulose acetate, compressible sugar, dextrate, dextrin, dextrose, ethylcellulose, fructose, isomalt, lactitol, lactose, mannitol, magnesium carbonate, magnesium oxide, maltodextrin, microcrystalline cellulose (MCC), polydextrose, sodium alginate, sorbitol, talc and xylitol.

In one embodiment, matrix constituent b. further comprises a binder, such as a binder selected from the group consisting of acacia, alginic acid, carbomers, carboxymethylcellulose sodium, carrageenan, cellulose, cellulose acetate phthalate, chitosan, copovidone, dextrate, dextrin, dextrose, ethylcellulose, gelatin, guar gum, hydroyethyl cellulose, hydroxyethylmethyl cellulose, hydroxypropyl cellulose (HPC), hydroxypropyl starch, hypromellose, methylcellulose, poloxamer, polydextrose, polyethylene oxide, povidone, sodium alginate, starch, pregelatinized starch, maltodextrin and synthetic polymers such as PVP (polyvinylpyrrolidone) and PEG (polyethylene glycol).

In one embodiment, matrix constituent b. further comprises a disintegrant, such as a disintegrant selected from the group consisting of alginic acid, calcium alginate, sodium alginate, carboxymethylcellulose calcium, carboxymethylcellulose sodium, croscarmellose sodium, crospovidone, guar gum, hydroxypropyl cellulose, magnesium aluminum silicate, methylcellulose, microcrystalline cellulose (MCC), polacrilin potassium, povidone, sodium starch glycolate starch or pregelatinized starch.

In one embodiment, matrix constituent b. further comprises a lubricant, such as a lubricant selected from the group consisting of calcium stearate, cooloidal silicon dioxide, glycerin monostearate, glyceryl behenate, glyceryl palmitostearate, hydrogenated castor oil, hydrogenated vegetable oil, magnesium lauryl sulfate, magnesium stearate, medium chain triglyceride, palmitic acid, polyethylene glycol, silicon dioxide, sodium lauryl sulfate, stearic acid, talc and zinc stearate.

Constituent b. in one embodiment comprises a HPMC and a 5HT1A agonist, such as buspirone. In a particular embodiment, the HPMC is Pharmacoat 603. The HPMC will in one embodiment be applied to constitute about 3% of the total contents of the dosage form (constituents a. and b.), such as between 0.1-10%, for example 0.1 to 1%, such as 1-2%, for example 2-3%, such as 3-4%, for example 4-5%, such as 5-6%, for example 6-7%, such as 7-8%, for example 8-9%, such as 9-10%.

In one embodiment, the excipient, such as HPMC, of constituent b. makes up of from 20-50% of the total contents of constituent b., such as from 20-30%, 30-40%, 40-50%.

In one embodiment constituent b. is a coating, such as a coating on an inner core matrix of constituent a. Said coating may be applied by coating or spraying of any kind known to the skilled person.

Constituent b. may also in one embodiment be in the form of a matrix, such as a solid matrix having immediate release characteristics. Such formulations are known to the skilled person.

Pharmaceutical Formulation—Components

In one embodiment the present invention provides a pharmaceutical formulation comprising
  a. a matrix constituent with extended release characteristics of an active pharmaceutical ingredient being an agonist of two or more of the 5-HT1B, 5-HT1D and 5-HT1F receptors,
  wherein said matrix comprises or consists of at least one release-controlling excipient, and an agonist of two or more of the 5-HT1B, 5-HT1D and 5-HT1F receptors.
  b. a constituent with immediate release characteristics of an active pharmaceutical ingredient being an agonist of the 5-HT1A receptor,
  wherein said constituent comprises or consists of at least one excipient, such as a film-forming excipient, and an agonist of the 5-HT1A receptor.

In one embodiment the present invention provides a pharmaceutical formulation comprising
  a. a matrix constituent with extended release characteristics of an active pharmaceutical ingredient being an agonist of two or more of the 5-HT1B, 5-HT1D and 5-HT1F receptors,
  wherein said matrix comprises or consists of at least one HPMC such as Methocel E4M and/or Methocel K100, one or more MCCs such as Avicel PH 101, talc, and an agonist of two or more of the 5-HT1B, 5-HT1D and 5-HT1F receptors.
  b. a constituent with immediate release characteristics of an active pharmaceutical ingredient being an agonist of the 5-HT1A receptor,
  wherein said constituent comprises or consists of at least one HPMC such as Pharmacoat 603 and an agonist of the 5-HT1A receptor.

In a particular embodiment, said matrix constituent a. is in the form of an inner core, and said constituent b. is in the form of an outer coating.

In a particular embodiment, the pharmaceutical formulation according to the present invention comprising constituents a. and b. comprises or consists of
  a. 20-40% HPMC, such as Methocel E4M and/or Methocel K100,
  b. 50-70% MCC, such as Avicel PH 101,
  c. 1-10% Talc,
  d. 0.1-10% of an agonist of two or more of the 5-HT1B, 5-HT1D and 5-HT1F receptors, preferably a triptan selected from the group consisting of zolmitriptan, rizatriptan, sumatriptan, naratriptan, almotriptan, frovatriptan and eletriptan,
  e. 1-20% of an agonist of the 5-HT1A receptor, preferably selected from the group consisting of buspirone, tandospirone, gepirone, alnespirone, binospirone, ipsapirone, perospirone, befiradol, repinotan piclozotan, osemozotan, flesinoxan, flibanserin and sarizotan,
  f. 0.1-10% HPMC, such as Pharmacoat 603,
  wherein components a., b., c. and d. are comprised in matrix constituent a., and components e. and f. are comprised in constituent b.

Consisting of may in this respect be taken to mean consisting essentially of.

In a further embodiment, the pharmaceutical formulation according to the present invention comprising constituents a. and b. comprises or consists of
  a. 25-35% HPMC, such as Methocel E4M and/or Methocel K100
  b. 55-65% MCC, such as Avicel PH 101
  c. 4-6% Talc
  d. 0.5-1% of an agonist of two or more of the 5-HT1B, 5-HT1D and 5-HT1F receptors, preferably a triptan selected from the group consisting of zolmitriptan, rizatriptan, sumatriptan, naratriptan, almotriptan, frovatriptan and eletriptan,
  e. 5-10% of an agonist of the 5-HT1A receptor, preferably selected from the group consisting of buspirone, tandospirone, gepirone, alnespirone, binospirone, ipsapirone, perospirone, befiradol, repinotan piclozotan, osemozotan, flesinoxan, flibanserin and sarizotan,
  f. 1-5% HPMC, such as Pharmacoat 603
  wherein components a., b., c. and d. are comprised in matrix constituent a., and components e. and f. are comprised in constituent b.

In a particular embodiment, the pharmaceutical formulation according to the present invention consisting of constituents a. and b. comprises or consists essentially or substantially of
  a. 27.24% HPMC, such as Methocel E4M
  b. 58.42% MCC, such as Avicel PH 101
  c. 4.54% Talc
  d. 0.61% zolmitriptan
  e. 6.12% buspirone
  f. 3.06% HPMC, such as Pharmacoat 603

In a particular embodiment, the pharmaceutical formulation according to the present invention consisting of constituents a. and b. has a weight of about 165.69 mg and comprises or consists essentially or substantially of
- a. 45.14 mg HPMC, such as Methocel E4M
- b. 96.80 mg MCC, such as Avicel PH 101
- c. 7.52 mg Talc
- d. 1 mg zolmitriptan
- e. 10.15 mg buspirone
- f. 5.07 mg HPMC, such as Pharmacoat 603

In one embodiment, matrix constituent a. of the pharmaceutical formulation comprises or consists of
- a. 10-50%, such as 20-40%, HPMC, such as Methocel E4M and/or Methocel K100
- b. 40-80%, such as 55-75% MCC, such as Avicel PH 101
- c. 1-10%, such as 2-8% talc
- g. 0.1-5%, such as 0.5-2% of an agonist of two or more of the 5-HT1B, 5-HT1D and 5-HT1F receptors, preferably a triptan selected from the group consisting of zolmitriptan, rizatriptan, sumatriptan, naratriptan, almotriptan, frovatriptan and eletriptan.

In a particular embodiment, matrix constituent a. of the pharmaceutical formulation comprises or consists essentially or substantially of
- a. 30% HPMC, such as Methocel E4M and/or Methocel K100
- b. 64.33% MCC, such as Avicel PH 101
- c. 5% talc
- d. 0.67% zolmitriptan In a particular embodiment, matrix constituent a. of the pharmaceutical formulation has a total weight of 150 mg and comprises or consists essentially or substantially of
- a. 45 mg HPMC, such as Methocel E4M and/or Methocel K100
- b. 96.5 mg MCC, such as Avicel PH 101
- c. 7.5 mg talc
- d. 1 mg zolmitriptan In one embodiment, the constituent b. of the pharmaceutical formulation comprises or consists of
- a. 25-40% HPMC, such as Pharmacoat 603
- b. 60-75% of an agonist of the 5-HT1A receptor, preferably selected from the group consisting of buspirone, tandospirone, gepirone, alnespirone, binospirone, ipsapirone, perospirone, befiradol, repinotan piclozotan, osemozotan, flesinoxan, flibanserin and sarizotan.

In a particular embodiment, the constituent b. of the pharmaceutical formulation comprises or consists essentially or substantially of
- a. 5 mg HPMC, such as Pharmacoat 603
- b. 10 mg buspirone.

Method of Preparation

The present invention provides methods for the preparation of the pharmaceutical formulation as defined herein. In one embodiment, the pharmaceutical formulation according to the present invention comprises an inner core matrix and an outer coating, and is manufactured by a process comprising the steps of
1) preparing granules by mixing (MCC and HPMC) with (HPMC and the agonist of two or more of the 5-HT1B, 5-HT1D and 5-HT1F receptors, such as zolmitriptan),
2) blending the granules of step 1) with talc,
3) compressing the talc granules of step 2) into a matrix tablet,
4) coating the matrix tablet of step 3) with a solution of (HPMC and an agonist of the 5-HT1A receptor such as buspirone), and
5) drying the coated matrix tablet of step 4).

Figure 8:
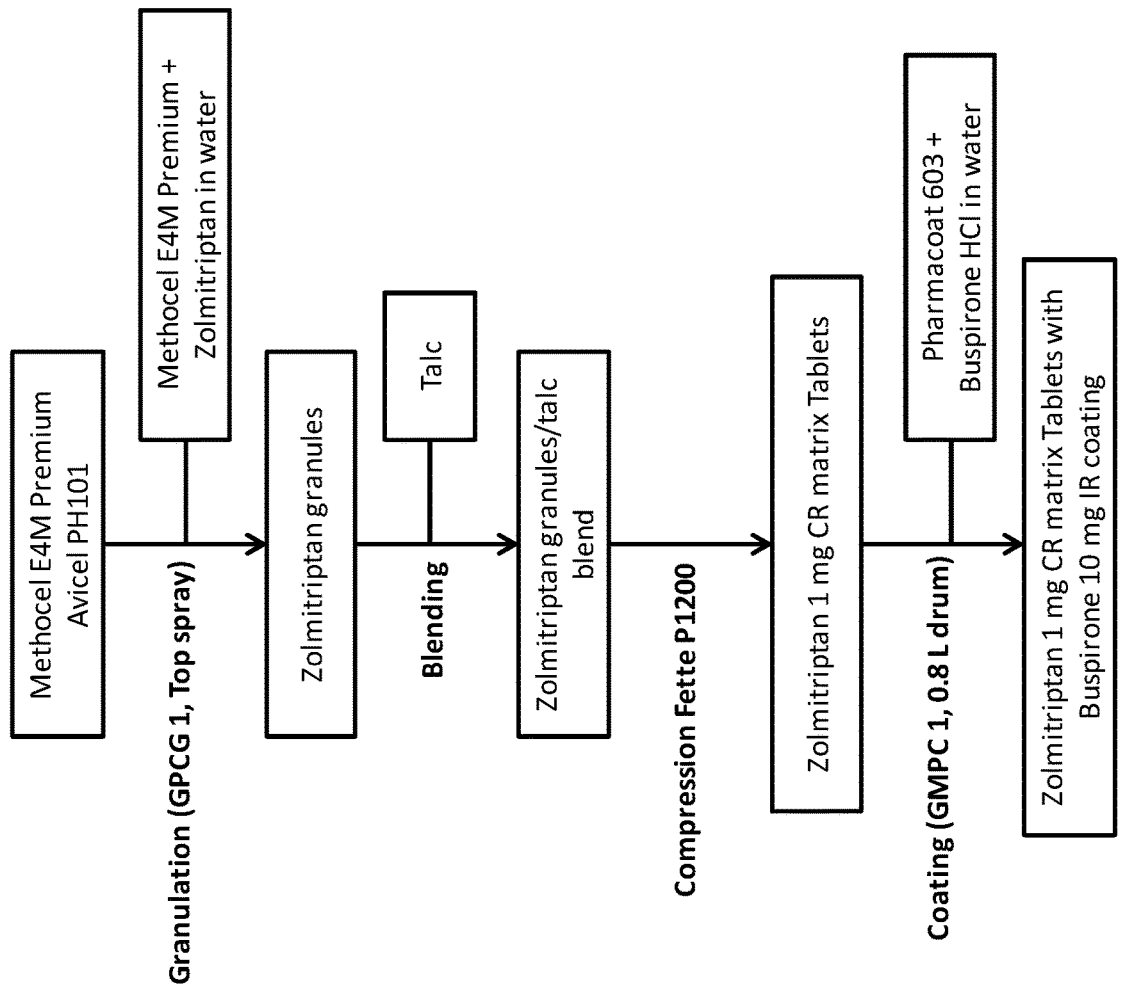
FIG. 8: The manufacturing process for the pre-clinical prototype of a fixed dose combination product according to the present invention (Zolmitriptan 1 mg CR inner core matrix tablets with Buspirone 10 mg IR outer coating; 0614/2012). See Example XI. CR=controlled release; IR=immediate release.

The manufacturing process for the formulation in the embodiment of an inner core ER (extended release) matrix and an outer coating IR (immediate release) is visualized in FIG. 8.

Manufacturing of capsules comprising granules or pellets of constituents a. and b. will be known to the skilled person.

Further Active Ingredients

The formulation or tablet of the present invention may be combined with or comprise one or more further active ingredients which are understood as other therapeutic compounds (active pharmaceutical ingredients) or pharmaceutically acceptable derivatives thereof.

A further active ingredient according to the present invention may be one or more agents selected from the group consisting of agents increasing the dopamine concentration in the synaptic cleft, dopamine, L-DOPA (e.g. levodopa) or dopamine receptor agonists or derivatives thereof. Thus, according to the present invention further active ingredients comprise dopamine receptor agonists, such as bromocriptine, pergolide, pramipexole, ropinirole, piribedil, cabergoline, apomorphine, lisuride, and derivatives thereof.

Further active ingredients may also be selected from the group of compounds which ameliorate PD symptoms or which are used for treatment of PD, such as peripheral inhibitors of the transformation of L-DOPA (or other dopamine prodrugs) to dopamine, for example carboxylase inhibitors such as carbidopa or benserazide, or NMDA antagonists such as for example amatidine (Symmetrel), catechol-O-methyl transferase (COMT) inhibitors such as for example tolcapone and entacapone, MAO-B inhibitors such as for example selegiline and rasagiline, serotonin receptor modulators, kappa opioid receptors agonists such as for example TRK-820 ((E)-N-[17-cyclopropylmethyl)-4, 5α-epoxy-3,14-dihydroxymorphinan-6β-yl]-3-(furan-3-yl)-N-methylprop-2-enamide monohydrochloride), GABA modulators, modulators of neuronal potassium channels such as flupirtine and retigabine, and glutamate receptor modulators.

In a preferred embodiment of the present invention, a further active ingredient is a dopamine prodrug, such as L-DOPA or a pharmaceutically acceptable derivative thereof. Thus in one preferred embodiment, L-DOPA is used in combination with a tablet comprising component i) and ii), such as zolmitriptan and buspirone.

In one embodiment of the present invention, the compounds or pharmaceutical compositions may be combined with two or more further active ingredients. Such two further active ingredients may be L-DOPA in combination with a carboxylase inhibitor.

Thus in an embodiment of the present invention, the two or more further active ingredients comprise L-DOPA and carbidopa, or L-DOPA and benserazide.

In another embodiment, such two further active ingredients are L-DOPA in combination with a COMT inhibitor, wherein the COMT inhibitor can be tolcapone, or entacapone.

The further active ingredients according to the present invention can also be included in the same formulations such as for example the L-DOPA/benserazide formulations sinemet, parcopa, madopar, or L-DOPA/COMT inhibitor formulations such as for example stalevo.

In a particular embodiment a pharmaceutical formulation according to the present invention, comprising a further active ingredient, is designed to slowly release the "triptan" by an extended release procedure while the 5-HT1A agonist is released at the same time or before the second active ingredient (e.g. L-DOPA) is released.

The further active ingredient may in one embodiment be present in the immediate release component (constituent b.) also comprising a 5-HT1A agonist, or may be in a separate component or layer, such as an additional coating. In another embodiment, the further active ingredient is present in the extended release component (matrix constituent a.) of the pharmaceutical formulation.

In a particular embodiment, the pharmaceutical formulation according to the present invention is to be administered in combination with a separate L-DOPA or L-DOPA/benzerazide preparation, simultaneously or sequentially. In a particular embodiment, said pharmaceutical formulation is administered before or simultaneously with treatment of the separate L-DOPA or L-DOPA/benzerazide preparation.

Kit of Parts

The present invention also provides for a kit of parts which can be useful for treatment of movement disorders as described herein.

A kit of parts according to the present invention comprises a pharmaceutical formulation as defined herein for treatment, prevention or alleviation of movement disorders. Kits according to the present invention allows for simultaneous, sequential or separate administration of the special formulation and one or more additional active ingredients as described herein.

In a preferred embodiment of the present invention, an additional active ingredient comprised in a kit provided by the invention is a dopamine prodrug, such as L-DOPA.

Movement Disorders

The present invention relates to a pharmaceutical formulation allowing for improved treatment of movement disorders, such as disorders which are associated with altered or impaired synaptic dopamine levels.

In one embodiment, the movement disorders according to the present invention is selected from the group consisting of Parkinson's disease, movement disorders associated with Parkinson's disease such as bradykinesia, akinesia and dyskinesia, L-DOPA induced dyskinesia, tardive dyskinesia, ataxia, akathisia, dystonia, essential tremor, Huntington's disease, myoclonus, Rett syndrome, Tourette syndrome, Wilson's disease, dyskinesias, chorea, Machado-Joseph disease, restless leg syndrome, spasmodic torticollis, geniospasm or movement disorders associated therewith, Movement disorders according to the present invention may also be associated with use of neuroleptic drugs, idiopathic disease, genetic dysfunctions, infections or other conditions which lead to dysfunction of the basal ganglia and/or lead to altered synaptic dopamine levels.

Parkinson's disease is associated with muscle rigidity, tremor, postural abnormalities, gait abnormalities, a slowing of physical movement (bradykinesia), and in extreme cases a loss of physical movement (akinesia). PD is caused by degeneration and death of dopaminergic neurons in substantia nigra pars compacta, and leads to dysfunctional regulation of dopamine neurotransmission.

In one particular embodiment of the present invention the movement disorder is Parkinson's disease or associated movement disorders akinesia, dyskinesia and bradykinesia, or movement disorders associated with Parkinson's disease such as L-DOPA induced dyskinesia. In one preferred embodiment of the present invention, the movement disorder is tardive dyskinesia.

In another embodiment of the present invention, the movement disorder is caused by or associated with medication of antipsychotics such as haloperidol, droperidol, pimozide, trifluoperazine, amisulpride, risperidone, aripiprazole, asenapine, and zuclopenthixol, antidepressants such as fluoxetine, paroxetine, venlafaxine, and trazodone, antiemetic drugs such as dopamine blockers for example metoclopramide (reglan) and prochlorperazine (compazine).

In yet another embodiment of the present invention, the movement disorder is caused by or associated with withdrawal of opioids, barbiturates, cocaine, benzodiazepines, alcohol, or amphetamines.

It is an aspect of the present invention to provide a pharmaceutical formulation as defined herein for use in a method for the treatment of a movement disorder.

It is an aspect of the present invention to provide a pharmaceutical formulation as defined herein for manufacture of a medicament for the treatment of a movement disorder.

In one embodiment, the pharmaceutical formulation as defined herein for use in a method for the treatment of a movement disorder is administered to an individual in need thereof.

An individual in need as referred to herein, is an individual that may benefit from the administration of a compound or pharmaceutical composition according to the present invention. Such an individual may suffer from a movement disorder or be in risk of suffering from a movement disorder. The individual may be any human being, male or female, infant, middle-aged or old. The movement disorder to be treated or prevented in the individual may relate to the age of the individual, the general health of the individual, the medications used for treating the individual and whether or not the individual has a prior history of suffering from diseases or disorders that may have or have induced movement disorders in the individual.

EXAMPLES

Example I

The 6-OHDA rat model as described below is useful for evaluation of 5-HT1 agonists for treatment of movement disorders associated with Parkinson's disease and LID. The 6-OHDA rat model was used in WO2012/048710 to show a synergistic effect of i.a. zolmitriptan and buspirone, and in PCT/DK2012/050190 to further show an additional positive effect of administering zolmitriptan before buspirone.

Present example 1 is included to show the additional positive effect of sequentially administering zolmitriptan before buspirone by injection.

The 6-OHDA Rat Model

6-OHDA (6-hydroxydopamine) is a neurotoxin that selectively kills dopaminergic and noradrenergic neurons and induces a reduction of dopamine levels in the brain. Administration of L-DOPA to unilaterally 6-OHDA-lesioned rats induces abnormal involuntary movements (AIMs). These are axial, limb and oral movements that occur only on the body side that is ipsilateral to the lesion. AIM rat models have been shown useful because they respond to a number of drugs which have been shown to suppress dyskinesia (including PD) in humans.

Test Procedure:

Animals: 90 experimentally-naïve, male, Sprague-Dawley rats at body weight of 200 to 250 g from Shanghai SLAC Co. Ltd. arrive at the laboratory at least 1 week prior to behavioural testing. Rats are housed in groups of n=2/cage. Animals have ad libitum access to standard rodent chow and water. Animal housing and testing rooms are maintained under controlled environmental conditions and are within close proximity of each other. Animal housing rooms are on a 12-hour light-dark cycle with lights on at 6:00 AM and maintained at 70° F./21° C. (range: 68-72° F./20-22° C.) with a humidity range of 20-40%. Testing rooms are maintained at 68-72° F. with a humidity range of 20-40%.

DA (dopamine)-denervating lesions are performed by unilateral injection of 6-OHDA in the ascending nigrostriatal pathway. Rats were anesthetized with pentobarbital sodium 40 mg/kg (i.p.) and positioned in a stereotactic frame. 6-OHDA is injected into the right ascending DA bundle at the following coordinates (in mm) relative to bregma and dural surface: (1) toothbar position −2.3, A=−4.4, L=1.2, V=7.8, (7.5 ug 6-OHDA), (2) toothbar position +3.4, A=−4.0, L=0.8, V=8.0mm (6 ug 6-OHDA). The neurotoxin injections are performed at a rate of 1 ul/min, and the injection cannula is left in place for an additional 2-3 min thereafter. Two weeks after surgery rats with nearly complete (>90%) lesions are selected by means of an amphetamine-induced rotation test. The animals are placed in plastic Perspex bowls (30 cm in diameter) and the rotational behavior (360° turns) is recorded by an automated rotometer for 90 min after the i.p. injection of 2.5 mg/kg d-amphetamine sulphate. Animals exhibiting 56 full body turns/min towards the side of the DA deficiency are included in the study. Animals are then allocated into two well-matched sub-groups (according to the amphetamine rotation) and receive daily treatment as described below.

Drugs and Treatment Regimens

Drug Treatment:

L-DOPA methyl ester (Sigma-Aldrich, Germany) is given at the dose of 6 mg/kg, combined with 15 mg/kg of benserazide HCl (Sigma-Aldrich, Germany). Chronic treatment with this dose of L-DOPA and benserazide is given for 3 weeks to all the rats with good lesions in order to induce a gradual development of dyskinetic-like movements. Thereafter, rats that have not developed dyskinesia are excluded from the study, and the rats with a cumulative AIM score ≥28 points over five testing sessions (dyskinesia severity grade ≥2 on each axial, limb and orolingual scores) are kept on a drug treatment regimen of at least two injections of L-DOPA/benserazide per week in order to maintain stable AIM scores. The selected rats are allocated groups of 9-12 animals each, which are balanced with the respect to AIM severity. The animals are then treated with the drug and drug combinations as described below.

Prevention:

In the prevention study rats are treated with L-DOPA methyl ester (6 mg/kg i.p. plus benserazide 15 mg/kg) in combination with buspirone (0.5-10 mg/kg) and zolmitriptan (0.5 mg/kg -20 mg/kg i.p.) for 3 weeks. At the end of this treatment (treatment period 1), animals received a low dose of apomorphine (0.02 mg/kg, s.c.) and tested for apomorphine-induced AIMs in order to investigate the sensitization state of the DA receptors. Treatments are then continued so that animals are treated only with L-DOPA for an additional two weeks (treatment period 2). Animals are injected daily and tested every second day for L-DOPA-induced dyskinesia throughout the experimental periods 1 and 2 and then sacrificed for HPLC analysis of DA, serotonin and metabolites.

To determine the effects of specific doses of a combination of buspirone and zolmitriptan the following group setting was used:

Vehicle: (saline, i.p., 30 min before L-DOPA, n=6)
Buspirone (0.5 mg/kg, intra peritoneally (i.p.), n=6)
Buspirone (0.5 mg/kg i.p.)+Zolmitriptan (From Damas-beta, Cat. No. TSP76106 Lot. No. T4903TSP76106,3 mg/kg i.p.)
Buspirone (0.5 mg/kg i.p.)+Zolmitriptan (10 mg/kg i.p.)
Buspirone (1 mg/kg i.p.)+Zolmitriptan (10 mg/kg i.p.)
Zolmitriptan was given 35 minutes before L-DOPA while buspirone was given 30 minutes before L-DOPA.

L-DOPA Induced AIMs and Drugs Screening Test

AIMs ratings are performed by an investigator who was kept unaware of the pharmacological treatment administered to each rat (experimentally blinded). In order to quantify the severity of the AIMs, rats are observed individually in their standard cages every 20th minute at 20-180 min after an injection of l-DOPA. The AIM's are classified into four subtypes:

(A) axial AIMs, i.e., dystonic or choreiform torsion of the trunk and neck towards the side contralateral to the lesion. In the mild cases: lateral flexion of the neck or torsional movements of the upper trunk towards the side contralateral to the lesion. With repeated injection of L-DOPA, this movement may develop into a pronounced and continuous dystonia-like axial torsion.

(B) limb AIMs, i.e., jerky and/or dystonic movements of the forelimb contralateral to the lesion. In mild cases: hyperkinetic, jerky stepping movements of the forelimb contralateral to the lesion, or small circular movements of the forelimb to and from the snout. As the severity of dyskinesia increases (which usually occurs with repeated administration of L-DOPA), the abnormal movements increase in amplitude, and assume mixed dystonic and hyperkinetic features. Dystonic movements are caused by sustained co-contraction of agonist/antagonist muscles; they are slow and force a body segment into unnatural positions. Hyperkinetic movements are fast and irregular in speed and direction. Sometimes the forelimb does not show jerky movements but becomes engaged in a continuous dystonic posture, which is also scored according to the time during which it is expressed.

(C) orolingual AIMs, i.e., twitching of orofacial muscles, and bursts of empty masticatory movements with protrusion of the tongue towards the side contralateral to the lesion. This form of dyskinesia affects facial, tongue, and masticatory muscles. It is recognizable as bursts of empty masticatory movements, accompanied to a variable degree by jaw opening, lateral translocations of the jaw, twitching of facial muscles, and protrusion of the tongue towards the side contralateral to the lesion. At its extreme severity, this subtype of dyskinesia engages all the above muscle groups with notable strength, and may also become complicated by self-mutilative biting on the skin of the forelimb contralateral to the lesion (easily recognizable by the fact that a round spot of skin becomes devoid of fur.

(D) locomotive AIMs, i.e., increased locomotion with contralateral side bias. The latter AIM subtype was recorded in conformity with the original description of the rat AIM scale, although it was later established that locomotive AIMs do not provide a specific measure of dyskinesia, but rather provide a correlate of contralateral turning behaviour in rodents with unilateral 6-OHDA lesions.

Each of the four subtypes are scored on a severity scale from 0 to 4, where 0=absent, 1=present during less than half of the observation time, 2=present for more than half of the observation time, 3=present all the time but suppressible by external stimuli, and 4=present all the time and not suppressible by external stimuli. Axial, limb and orolingual AIMs are found to be modulated in a similar way by all the tested substances.

Figure 2:
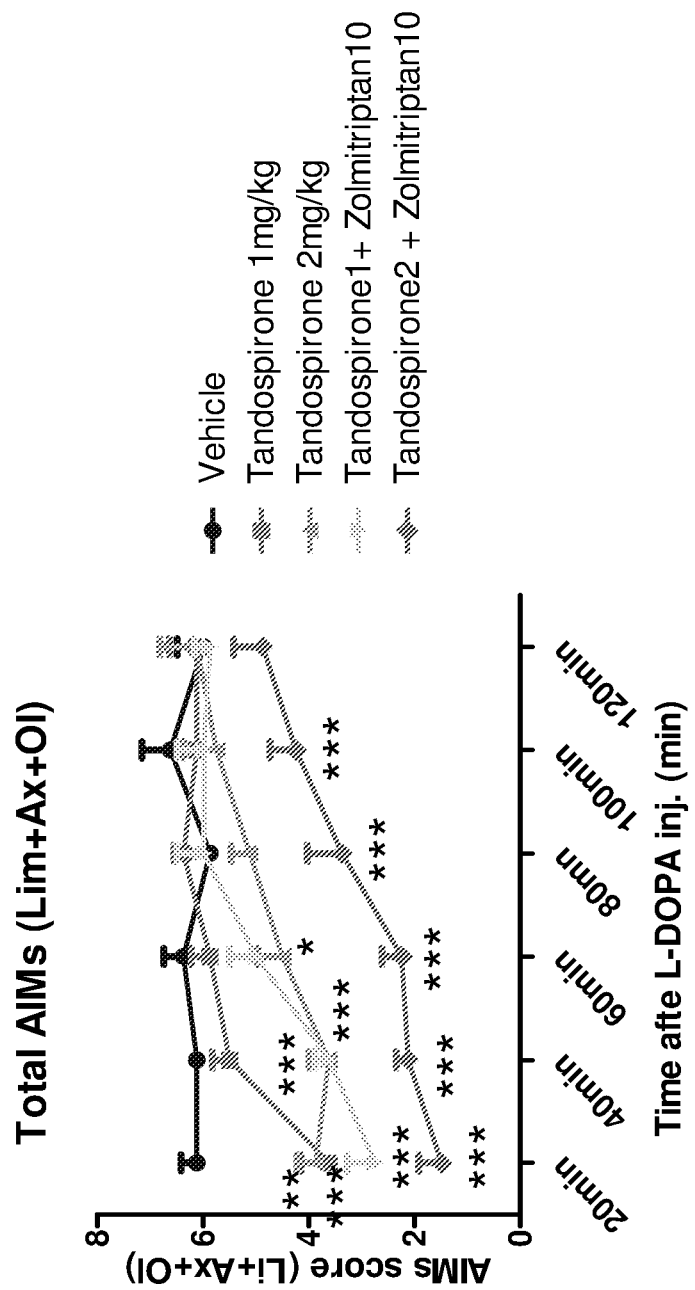
FIG. 2: The time course showing effect of tandospirone and combination of tandospirone and zolmitriptan on L-DOPA induced AIMs (Lim+Ax+Ol). *: P<0.001, : P<0.01,*: P<0.05 , two way ANOVA followed by Bonferroni post-tests compared with vehicle control at each time point. Detailed in Example II.

Rats were tested for AIMs using the sum of locomotive (LO) oraxial (AX), limb (LI), and orolingual (OL) AIM scores per testing session for statistical analyses. The results of the drug screening test are presented in FIG. 2 and showed that buspirone (0.5 mg/kg i.p.) in combination with zolmitriptan (3 mg/kg i.p. or 10 mg/kg i.p) or buspirone (1.0 mg/kg i.p.) in combination with zolmitriptan (10 mg/kg i.p) significantly reduced L-DOPA-induced dyskinesia. When given alone buspirone (0.5 mg/kg i.p.) only partly reduced AIM.

Example II

The present study describes the evaluation of zolmitriptan and tandospirone in the 6-OHDA rat model.

Animals: 67 Sprague-Dawley male rats (bred in house, originally from SLAC Laboratory Animal Co. Ltd) at 9-week of age at body weight of 200 to 250 g from Shanghai SLAC Co. Ltd. arrived at the laboratory at least 1 week prior to behavioural testing. Rats were housed in groups of n=2/cage. Animals had ad libitum access to standard rodent chow and water. Animal housing and testing rooms were maintained under controlled environmental conditions and were within close proximity of each other. Animal housing rooms were on a 12-hour light-dark cycle with lights on at 6:00 AM and maintained at 70° F./21° C. (range: 68-72° F./20-22° C.) with a humidity range of 20-40%. Testing rooms were maintained at 68-72° F. with a humidity range of 20-40%.

6-OHDA lesion surgery: Dopamine (DA)-denervating lesions were performed by unilateral injection of 6-OHDA in the ascending nigrostriatal pathway as detailed in Example I. After recovery from surgery, rats with nearly complete (>90%) lesions were selected by means of an apomorphine-induced rotation test. I.p. injection of 0.5 mg/kg apomorphine-HCl (Sigma) in saline evoked contralateral turning, which is considered to be the result of de-nervated hypersensitivity of DA receptors in the lesion side. Rotational behaviour in response to DA agonists grossly correlates with the severity of the lesion. Quantification of the rotational response was accomplished in rats by counting the turns in 30 minutes. Rat with rotational score≥6 turns/min were selected for next tests. Animals were then allocated into two well-matched sub-groups (according to the amphetamine rotation) and received daily treatment as described below.

Drugs and treatment regimens: L-DOPA methyl ester combined with benserazide HCl was administered as detailed in Example I.

L-DOPA Induced AIMs and Drugs Screening Test

Rats were tested for AIMs as described above in Example I. To determine the effects of specific doses of a combination of tandospirone and zolmitriptan the following group setting was used:

1. L-DOPA 6 mg/kg (20 min before test); Vehicle: (10% tween80, i.p., 30 min before test, n=8)
2. L-DOPA 6 mg/kg (20 min before test); tandospirone (1 mg/kg, i.p., 30 min before test, n=8)
3. L-DOPA 6 mg/kg (20 min before test); tandospirone (2 mg/kg, i.p., 30 min before test, n=8)
4. L-DOPA 6 mg/kg (20 min before test); tandospirone (1 mg/kg, i.p., 30 min before test, n=8)+zolmitriptan (10 mg/kg, i.p., 30 min before test, n=8)
5. L-DOPA 6 mg/kg (20 min before test); tandospirone (2 mg/kg, i.p., 30 min before test, n=8)+zolmitriptan (10 mg/kg, i.p., 30 min before test, n=8)

The rats were allocated randomly to 5 groups, which were balanced with their total AIM score from pre-screening test.

Figure 3:
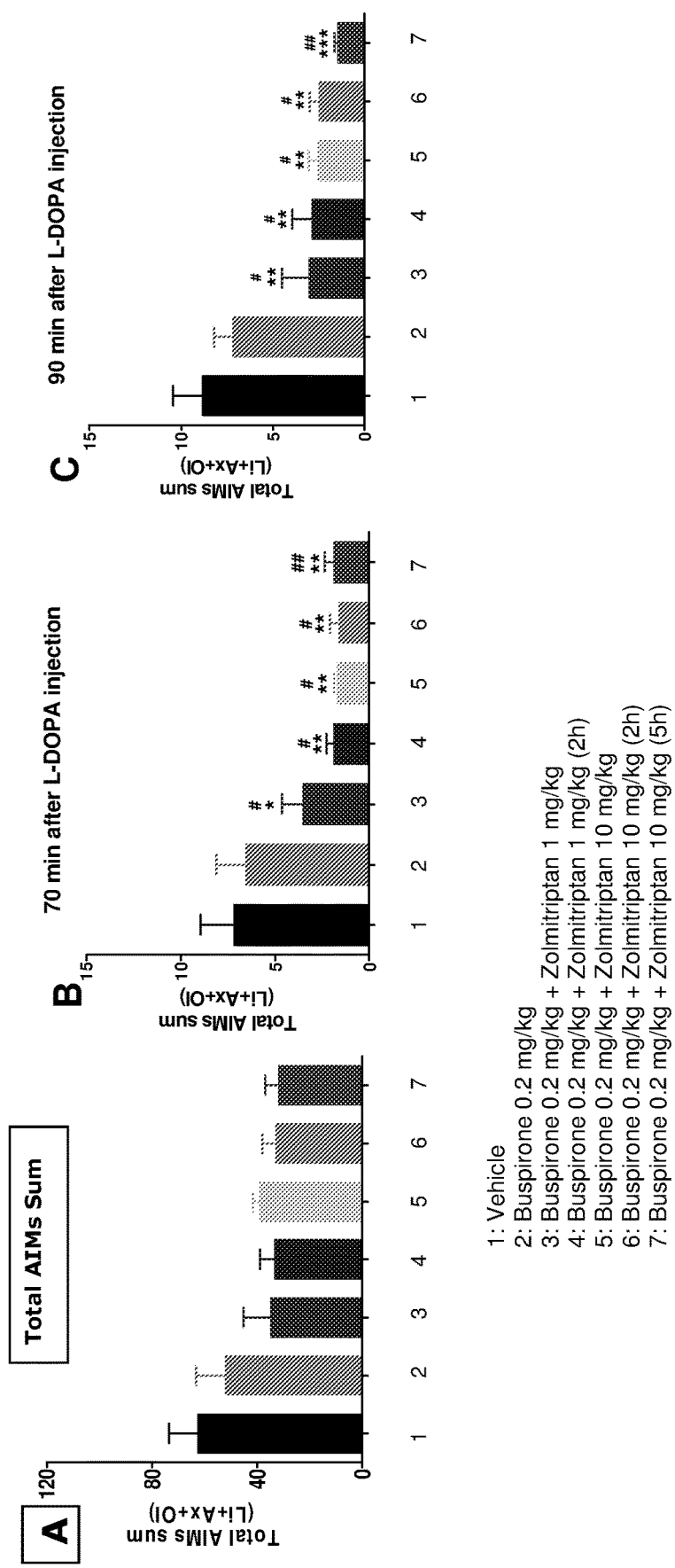
FIG. 3: Effect of combination of buspirone and zolmitriptan on L-DOPA induced abnormal involuntary movements (AIMs) in rats. A) Total AIMs (Lo, Li, Ax, Ol) sum post treatments (all time points). Zolmitriptan was dosed 11 min, 2 hr or 5 hr before AIMs ratings by s.c. injection. The mixture of L-DOPA (8 mg/kg) and benserazide (15 mg/kg) was dosed 10 min before AIMs ratings. N=6-7. B) Total AIMs at 70 min after L-DOPA injection. C) Total AIMs at 90 min after L-DOPA injection. Data were expressed as Mean±SEM, *p<0.001, p<0.01, *p<0.05 vs. vehicle group, ##p<0.01, #p<0.05, vs. Bus 0.2 mg/kg, one way ANOVA, Newman-Keuls test, n=6~7. The figure shows that the combination of buspirone and zolmitriptan has superior effect to buspirone alone, which effect is improved when zolmitriptan is administered before buspirone. Detailed in Example III.

The results of the drug screening test are presented in FIG. 3 and showed that tandospirone (1 mg/kg i.p. and 2 mg/kg i.p.) partially and briefly reduce AIMs while a combination between that tandospirone (1 mg/kg i.p. and 2 mg/kg i.p.) with zolmitriptan (10 mg/kg i.p.) significantly reduced L-DOPA-induced dyskinesia with a prolonged duration of action.

Example III

The present study describes the evaluation of zolmitriptan and buspirone in the 6-OHDA rat model, administered simultaneously or sequentially.

Animals: 45 Sprague-Dawley male rats (bred in house, originally from SLAC Laboratory Animal Co. Ltd) at body weight of 390-535 g were housed in groups of n=2/cage. Animals had ad libitum access to standard rodent chow and water.

The dosing procedure was performed by appointed scientists who were not involved in the AIMs ratings. Zolmitriptan was dosed 11 min, 2 h, and 5 h before AIMs ratings by s.c. injection individually according to the group setting. Buspirone was dosed 11 min before AIMs ratings by s.c. injection. The mixture of L-DOPA (8 mg/kg) and Benserazide (15 mg/kg) was dosed 10 min before AIMs ratings. S.c. injections were on each sides of the back of the rats.

AIMs ratings were performed as detailed in Example I. For each rat, a score was given to each AIMs subtype (Lo, Li, Ax and Ol) at each time point. The total AIMs were summed from scores of Li, Ax and Ol in each time point. The total AIMs sum was calculated by summing the total AIMs of all time points. Data were expressed as mean±SEM and analyzed with one way ANOVA followed by post hoc Newman-Keuls tests or unpaired t tests. Data were analyzed and graphed by Graph Pad Prism 5.

Example IV

The present study describes the evaluation of zolmitriptan and tandospirone in the 6-OHDA rat model as described in Example I & II.

L-DOPA Induced AIMs and Drugs Screening Test

Rats are tested for AIMs as described above in Example I. To determine the effects of time of administration of combinations of tandospirone and zolmitriptan the following group setting is used:

1. L-DOPA (6 mg/kg s.c., 20 min before test); Vehicle: (10% tween80, i.p., 30 min before test, n=8).
2. L-DOPA (6 mg/kg s.c., 20 min before test); tandospirone (2 mg/kg, i.p., 25 min before test, n=8)+zolmitriptan (10 mg/kg, i.p., 60 min before test, n=8).
3. L-DOPA (6 mg/kg s.c., 20 min before test); tandospirone (2 mg/kg, i.p., 25 min before test, n=8)+zolmitriptan (3 mg/kg, i.p., 60 min before test, n=8).
4. L-DOPA (6 mg/kg s.c., 20 min before test); tandospirone (2 mg/kg, i.p., 25 min before test, n=8)+zolmitriptan (3 mg/kg, i.p., 25 min before test, n=8).

The rats are allocated randomly to 4 groups, which are balanced with their total AIM score from pre-screening test.

The results of the drug screening test show that tandospirone (2 mg/kg i.p.) in combination with zolmitriptan (10 mg/kg i.p.) significantly reduced L-DOPA-induced dyskinesia in particularly when zolmitriptan is added before tandospirone.

Example V

The present study describes the evaluation of zolmitriptan and buspirone in the 6-OHDA rat model as described in Example I & II.

L-DOPA Induced AIMs and Drugs Screening Test

Rats are tested for AIMs as described above in Example I. To determine the effects of time of administration of combinations of buspirone and zolmitriptan the following group setting is used:

1. L-DOPA (6 mg/kg, s.c., 20 min before test); Vehicle: (10% tween80, s.c., 25 min before test, n=6).
2. L-DOPA (6 mg/kg, s.c., 20 min before test); buspirone (0.5 mg/kg, s.c., 25 min before test, n=6)+zolmitriptan (3 mg/kg, s.c., 45 min before test, n=6).
3. L-DOPA (6 mg/kg, s.c., 20 min before test); buspirone (0.5 mg/kg, s.c., 25 min before test, n=6)+zolmitriptan (3 mg/kg, s.c., 60 min before test, n=6).
4. L-DOPA (6 mg/kg, s.c., 20 min before test); buspirone (0.5 mg/kg, s.c., 25 min before test, n=6)+zolmitriptan (3 mg/kg, s.c., 25 min before test, n=6).

The rats are allocated randomly to 4 groups, which are balanced with their total AIM score from pre-screening test.

The results of the drug screening test show that that tandospirone (0.5 mg/kg s.c.) in combination between with zolmitriptan (3 mg/kg i.p.) significantly reduced L-DOPA-induced dyskinesia in particularly when zolmitriptan is added before tandospirone.

Example VI

The present study describes the evaluation of sustained release of zolmitriptan and either buspirone or tandospirone in the 6-OHDA rat model as described in Example I.

To determine the effects of sustained and continuous release of zolmitriptan in combinations with either buspirone or tandospirone the following treatments are performed:

The rats are allocated randomly to 5 groups, which are balanced with their total AIM score from pre-screening test.

Adult rats are infused with continuous administration of zolmitriptan via an Alzet® minipump placed subcutaneously in the neck. The pump is filled with zolmitriptan or vehicle according to the Manufacturer's instructions allowing a continuous flow of drug in the range of 10-50 mg/kg for 14 days. The effect of the release is tested as described in example xx, and specified below:

1. L-DOPA (6 mg/kg, s.c., 20 min before test); Vehicle: (10% tween80, s.c., 25 min before test, n=6).
2. L-DOPA (6 mg/kg, s.c., 20 min before test); buspirone (0.25 mg/kg, s.c., 25 min before test, n=6).
3. L-DOPA (6 mg/kg, s.c., 20 min before test); buspirone (0.5 mg/kg, s.c., 25 min before test, n=6)
4. L-DOPA (6 mg/kg s.c., 20 min before test); tandospirone (1 mg/kg, i.p., 25 min before test, n=6)
5. L-DOPA (6 mg/kg s.c., 20 min before test); tandospirone (2 mg/kg, i.p., 25 min before test, n=6).

The results of the drug screening test show that that both buspirone and tandospirone in doses described above significantly reduced L-DOPA-induced dyskinesia and that the effect in animals with steady infusion of zolmitriptan via subcutaneously placed mini-pumps had a larger benefit in terms of reduction in AIMs.

Example VII

The present study describes the evaluation of rizatriptan and buspirone in the 6-OHDA rat model as described in Example I & II.

L-DOPA Induced AIMs and Drugs Screening Test

Rats are tested for AIMs as described above in Example I.

To determine the effects of time of administration of combinations of buspirone and rizatriptan the following group setting is used:

1. L-DOPA 6 mg/kg+15 mg/kg benserazide, s.c.10 min before test;
2. Buspirone 0.35 mg/kg, s.c; L-DOPA 6 mg/kg+15 mg/kg benserazide, sc; all compounds 10 min before test.
3. Buspirone 0.35 mg/kg, s.c.+rizatriptan 10 mg/kg,s.c; L-DOPA 6 mg/kg+15 mg/kg benserazide, s.c.; all compounds 10 min before test.
4. Rizatriptan 3 mg/kg, s.c., 2 hr before test+Buspirone 0.35 mg/kg,s.c.,10 min before test; L-DOPA 6 mg/kg+15 mg/kg benserazide, s.c.; 10 min before test.

The rats are allocated randomly to 4 groups, which are balanced with their total AIM score from pre-screening test.

The results of the drug screening test show that rizatriptan in combination with buspirone reduces L-DOPA-induced dyskinesia and that rizatriptan administered before buspirone reduces AIMs.

Example VIII

The combined formulation of extended release of an agonist of the 5HT1B, 5-HT1D and/or 5-HT1F receptor and immediate-release of a 5-HT1A receptor agonist may be tested.

To determine the potential for a dosing regimen according to the present invention, the formulations may be administered to rats in preclinical models of movement disorders such as L-DOPA induced dyskinesia. One model hereof is the 6-OHDA induced rat model of Parkinson's disease wherein dyskinesia is determined by measuring abnormal involuntary movements (AIM).

One way to assess the potential of an extended release formulation of an agonist of the 5HT1B, 5-HT1D and/or 5-HT1F receptor is to dose the agonist (e.g. zolmitriptan) well in advance of the 5-HT1A agonist (e.g. buspirone) (e.g 2-5 hrs) so that the 'tail' of the elimination curve of e.g. zolmitriptan mimics the flat and low dose release from an extended release formulation.

Another way to determine the potential for such a dosing regimen is to dose the agonist of the 5HT1B, 5-HT1D and/or 5-HT1F receptor (e.g. zolmitriptan) by continuous administration via a pump (such as an Alzet®minipump) placed subcutaneously in the neck of the rats of the in the 6-OHDA rat model of L-DOPA induced dyskinesia. The pump is filled with the 5-HT1B/D/F agonist (e.g. zolmitriptan) according to the Manufacturer's instructions allowing a continuous flow of drug in the range of 0.5-50 mg/kg/day for 14 days. The 5-HT1A agonist is added by dosing the compound by e.g. iv, po, or sc administration, and the combined effects tested (i.e. effect on ATMs).

The plasma concentration of both drugs may readily be measured by conventional techniques.

For the combined formulations of extended release of an agonist of the 5HT1B, 5-HT1D and/or 5-HT1F receptor and immediate-release of an 5-HT1A receptor agonist, it may be determined that the concentration of the agonist of the 5HT1B, 5-HT1D and/or 5-HT1F receptor is relatively steady state and low, and that the concentration of the 5-HT1A receptor agonist is a bolus or peak.

Example IX

The plasma concentrations as a function of time after administration of the drugs of the present invention can be determined by pharmacokinetic studies.

Male Sprague-Dawley rats (200-300 g) are used for the pharmacokinetic studies, following acclimatization for 5 days after arrival.

Buspirone (0.04 mg/mL) and zolmitriptan (2.0 mg/mL) are dissolved in separate formulations consisting of aqueous 10% hydroxyl-propyl beta cyclodextrin, pH 6. Zolmitriptan (10 mg/kg) is administered s.c. to the rats at time 0 min and Buspirone (0.2 mg/kg) is subsequently dosed s.c. at time 30 min.

Plasma concentration-time profiles of buspirone and zolmitriptan are determined from blood samples drawn serially from a catheter surgically implanted in the carotid artery in rats. Following administration of zolmitriptan, 9 serial blood samples (~200 μL) are taken from each rat at time 10, 20, 30, 45, 60, 120, 180, 240, 360 min.

Blood samples are collected in EDTA-coated tubes and centrifuged for 10 min at 4° C. after which plasma is transferred to fresh vials and stored at −80° C.

Quantification of buspirone and zolmitriptan is performed with liquid chromatography, tandem mass spectrometry (LC-MS/MS). A standard curve consists of 8 calibration standards (1-500 ng/ml for buspirone and 1-3000 ng/ml for zolmitriptan, respectively) for the LC-MS/MS method used for quantification.

Example X

Development and Evaluation of a Fixed Dose Combination Product

The aim of the work was to develop a fixed dose combination product with a controlled release (CR) core matrix tablet containing 1 mg zolmitriptan (drug release profile up to 12 hours), and an immediate release (IR) 10 mg buspirone dose in the tablet film-coat. The development of the CR zolmitriptan granulation and tabletting was performed in parallel to the development of the buspirone IR coating.

The manufacturing process comprised several manufacturing steps with intermediate products (granulation, blending, tabletting and coating), each product having a batch number as described in table 1, and a composition as outlined in table 2 (uncoated zolmitriptan tablets) and table 3 (coated zolmitriptan tablets):

TABLE 1

Correspondence table between batches from the different manufacturing steps.

| Manuf. step: | | | |
|---|---|---|---|
| Granulation | Blending | Tabletting | Coating |
| Batch numbers | | | |
| — | — | 0408/2012* | 0475/2012 |
| — | — | 0408/2012* | 0476/2012 |
| — | — | 0408/2012* | 0477/2012 |
| 0489/2012 | — | — | — |
| 0492/2012 | — | — | — |
| 0493/2012 | 0509/2012 | 0510/2012 | — |
| 0430/2012 | 0532/2012 | 0533/2012 | — |
| 0531/2012 | 0534/2012 | 0535/2012 | — |
| 0545/2012 | 0549/2012 | 0550/2012 | — |
| 0546/2012 | 0551/2012 | 0552/2012 | — |
| 0547/2012 | 0553/2012 | 0554/2012 | 0584/2012 |
| 0548/2012 | 0555/2012 | 0556/2012 | 0585/2015 |
| 0573/2012 | 0574/2012 | 0575/2012 | 0586/2012 |
| 0576/2012 | 0577/2012 | 0578/2012 | 0587/2012 |
| 0590/2012 | 0612/2012 | 0613/2012 | 0614/2012 |

*Placebo tablets (121 mg) in stock at manufacturer (Glatt)

TABLE 2

Composition of the uncoated Zolmitriptan tablets tested in dissolution

| Ingredients | 0510/2012 (%) | 0533/2012 (%) | 0535/2012 (%) | 0550/2012 (%) | 0552/2012 (%) | 0554/2012 (%) | 0556/2012 (%) | 0575/2012 (%) | 0578/2012 (%) | 0613/2012 (%) |
|---|---|---|---|---|---|---|---|---|---|---|
| Methocel K100 Premium | 50.00 | — | 25.00 | 30.00 | 35.00 | — | — | — | — | — |
| Pharmacoat 603 | — | 25.00 | — | — | — | — | — | — | — | — |
| Methocel E4M Premium | — | — | — | — | — | 25.00 | 30.00 | 40.00 | 50.00 | 30.00 |
| Avicel PH 101 | 44.33 | 69.33 | 69.33 | 64.33 | 59.33 | 69.33 | 64.33 | 54.33 | 44.33 | 64.33 |
| Zolmitriptan | 0.67 | 0.67 | 0.67 | 0.67 | 0.67 | 0.67 | 0.67 | 0.67 | 0.67 | 0.67 |
| Talc | 5.00 | 5.00 | 5.00 | 5.00 | 5.00 | 5.00 | 5.00 | 5.00 | 5.00 | 5.00 |
| Total | 100.00 | 100.00 | 100.00 | 100.00 | 100.00 | 100.00 | 100.00 | 100.00 | 100.00 | 100.00 |

| Ingredients | 0510/2012 (mg) | 0533/2012 (mg) | 0535/2012 (mg) | 0550/2012 (mg) | 0552/2012 (mg) | 0554/2012 (mg) | 0556/2012 (mg) | 0575/2012 (mg) | 0578/2012 (mg) | 0613/2012 (mg) |
|---|---|---|---|---|---|---|---|---|---|---|
| Methocel K100 Premium | 75.00 | 0.00 | 37.50 | 45.00 | 52.50 | — | — | — | — | — |
| Pharmacoat 603 | — | 37.50 | — | — | — | — | — | — | — | — |
| Methocel E4M Premium | — | — | — | — | — | 37.50 | 45.00 | 60.00 | 75.00 | 45.00 |
| Avicel PH 101 | 66.50 | 104.00 | 104.00 | 96.50 | 89.00 | 104.00 | 96.50 | 81.50 | 66.50 | 96.50 |
| Zolmitriptan | 1.00 | 1.00 | 1.00 | 1.00 | 1.00 | 1.00 | 1.00 | 1.00 | 1.00 | 1.00 |
| Talc | 7.50 | 7.50 | 7.50 | 7.50 | 7.50 | 7.50 | 7.50 | 7.50 | 7.50 | 7.50 |
| Total* | 150.00 | 150.00 | 150.00 | 150.00 | 150.00 | 150.00 | 150.00 | 150.00 | 150.00 | 150.00 |

*target weight of the manufactured tablets (mg)

TABLE 3

Composition of the placebo or Buspirone coated Zolmitriptan tablets tested in dissolution

| Ingredients | Batch numbers | | | | |
|---|---|---|---|---|---|
| | 0584/ 2012 (%) | 0585/ 2012 (%) | 0586/ 2012 (%) | 0587/ 2012 (%) | 0614/ 2012** (%) |
| Pharmacoat 603 | 3.20 | 2.95 | 2.94 | 3.22 | 3.06 |
| Methocel E4M Premium | 24.20 | 29.12 | 38.82 | 48.39 | 27.24 |
| Avicel PH 101 | 67.12 | 62.44 | 52.73 | 42.90 | 58.42 |
| Talc | 4.84 | 4.85 | 4.85 | 4.84 | 4.54 |
| Zolmitriptan | 0.65 | 0.65 | 0.65 | 0.65 | 0.61 |
| Buspirone | — | — | — | — | 6.12 |
| Total | 100.00 | 100.00 | 100.00 | 100.00 | 100.00 |

| Ingredients | Batch numbers | | | | |
|---|---|---|---|---|---|
| | 0584/ 2012 (mg) | 0585/ 2012 (mg) | 0586/ 2012 (mg) | 0587/ 2012 (mg) | 0614/ 2012 (mg) |
| Pharmacoat 603 | 4.98 | 4.53 | 4.52 | 5.05 | 5.07 |
| Methocel E4M Premium | 37.67 | 44.74 | 59.63 | 75.80 | 45.14 |
| Avicel PH 101 | 104.48 | 95.93 | 80.99 | 67.21 | 96.80 |
| Talc | 7.53 | 7.46 | 7.45 | 7.58 | 7.52 |
| Zolmitriptan | 1.00 | 0.99 | 0.99 | 1.01 | 1.00 |
| Buspirone | — | — | — | — | 10.15 |
| Total*** | 155.67 | 153.65 | 153.59 | 156.65 | 165.69 |

**prototype 1 shipped for monkey studies
***average weight of the coated tablets at the end of the coating process (including drying of the coated tablets)

Development of the CR Zolmitriptan Granules and Corresponding Tablets:

The development strategy to obtain an appropriate CR zolmitriptan profile consisted in manufacturing first zolmitriptan granules containing the API (active pharmaceutical ingredient) combined with microcrystalline cellulose (MCC, Avicel PH101 grade) and hydroxypropylmethylcellulose (HPMC) and to compress the obtained granules into a matrix tablets with 5% talc.

To design an appropriate drug release rate for zolmitriptan different HPMC grades exhibiting different viscosity (Pharmacoat 603, Methocel K100 and Methocel E4M) were tested in different quantities. Only one single HPMC grade was tested each time in a formulation.

The spray suspensions used for the granulation processes were containing a small fraction of the HPMC quantity to be present in the final granules or tablets. Except for placebo granulation the entire zolmitriptan quantity was dispersed each time together with HPMC in the spray suspensions. The HPMC/zolmitriptan suspensions were sprayed on the blends containing the MCC and the rest of HPMC (always of the same grade than the one added in the spray suspension). The amount of liquid sprayed was calculated before the process to reach a pre-determined composition in the final dried granules and in the corresponding tablets. Each granule formulation was designed to obtain after blending with talc a precise matrix tablet composition (i.e. containing 25%, 30%, 35%, 40% or 50% HPMC of the final tablets weight).

The development of the zolmitriptan granulation process was started by performing two placebo granulation pre-trials using 35% Methocel K100 (first batch 0489/2012 and optimization batch 0492/2012). The main objective of these pre-trials was to determine the correct process parameters for the next granulation trials.

The first granulation process with zolmitriptan present in the spray dispersion (batch 0493/2012) was performed by targeting ~50% of Methocel K100 in the final granules. The particle size distribution (PSD) of the final product exhibited a D50~140 μm. The granules were blended afterwards with 5% talc and compressed into tablets (batch 0510/2012) with the following hardness: 39N, 65N and 98N. The drug release rates of all the tablets were too slow with less than 20% release in each tablet hardness case and a nearly flat profile for the 98N tablets.

Consequently a new granulation batch (0530/2012) was manufactured with a lower amount of Methocel K100 (25%) to increase the drug release rate from the final matrix tablet. A similar granulation was performed with the same amount but using a different grade of HPMC, i.e. Pharmacoat 603 (batch 0531/2012).

Figure 5:
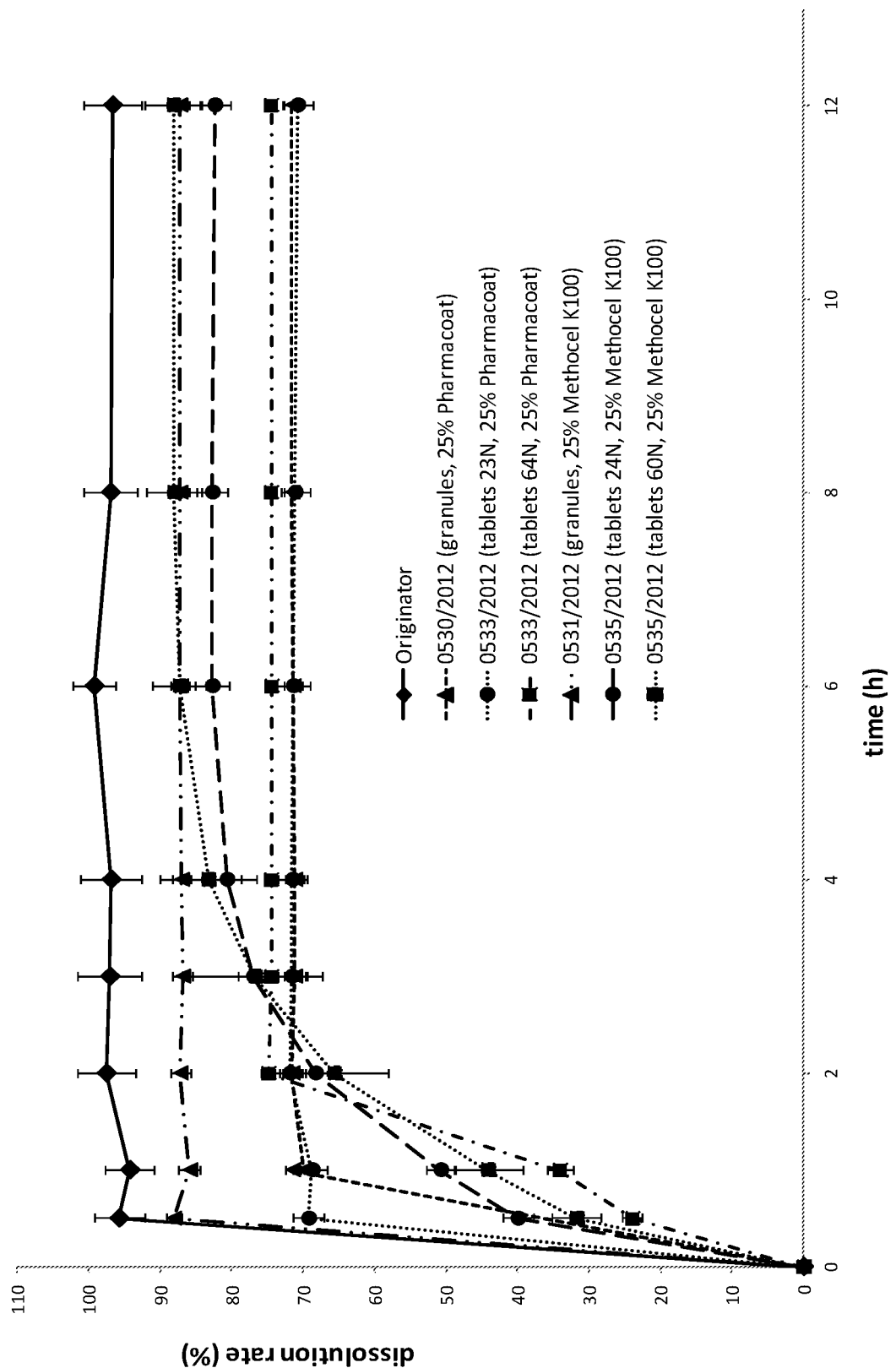
FIG. 5: Dissolution profiles of the current marketed tablet comprising zolmitriptan alone ('originator') for comparison and the produced zolmitriptan granules and tablets with varying parameters. Numbers (e.g. 0533/2012) refer to internal batch number (see Example 9). Dissolution rate % refers to amount of active pharmaceutical ingredient released in a dissolution assay.

The dissolution profiles of the 2 new granules batches and of their corresponding tablets (batches 0533/2012 and 0535/2012 respectively) exhibited significantly faster release rate than for the previous batch 0510/2012 containing 50% Methocel K100. Furthermore a rate decrease could be observed between the granules profiles and the corresponding tablets profiles (except for the 23N tablets batch 0533/2012) (FIG. 5). This decrease in release rate corresponds to the establishment of a MCC/HPMC matrix within the tablet during the compression.

The zolmitriptan release rate of the -60N tablets batches 0533/2012 and 0535/2012 were too fast. Furthermore all tablets disintegrated during the dissolution testing. This disintegration may have a negative impact on the release control of the Zolmitriptan as it induced an increase of the relative surface area are between the disintegrated matrix particles and the dissolution medium.

The maximum release was up to 90% in the case of tablets containing Methocel K100 (batch 0535/2012) and up to 70% in the case of tablets containing Pharmacoat 603 (batch 0533/2012). These values were well-correlated with the low assay results obtained for the granules and the tablets.

For the next trials Pharmacoat 603 was excluded as a component of the future matrix tablets prototype because of the low maximum release observed for the batch 0533/2012 (25% Pharmacoat 603 in the tablets). Instead, different formulations containing Methocel K100 or E4M were designed to obtain a compromise between the two extreme release rates obtained up to now with 50% and 25% HPMC in the tablets.

Thus new granules containing ~30% Methocel K100 (batch 0545/2012) and ~35% Methocel K100 (batch 0546/2012) were manufactured and compressed into ~60N tablets (batches 0550/2012 and 0552/2012 respectively). Additionally another HPMC grade was tested by manufacturing new granules containing ~25% Methocel E4M (batch 0547/2012) and ~30% Methocel E4M (batch 0548/2012). The granules were compressed with talc into ~60N tablets (batches 0554/2012 and 0556/2012 respectively). The dissolution profile of the tablets containing 30% and 35% Methocel K100 exhibited still a too fast release rate which was however slower than the rate from tablets batch 0535/2012 (25% Methocel K100). Moreover the drug release was significantly faster than the release from tablets batch 0510/2012 (50% Methocel K100).

For the tablets containing Methocel E4M the release profiles were satisfying with approximately 90% zolmitriptan release after 12H for the batch 0554/2012 which contains 25% of the polymer (curve included in FIG. 6), and more than 85% after 12H for the batch 0556/2012 with 30% of Methocel E4M. Furthermore the tablets containing Methocel E4M did not disintegrate during dissolution testing. Considering all these points Methocel E4M was seen as the most promising HPMC grade and was selected for further development trials.

In order to increase further the retard effect of zolmitriptan during the first hours of the release new granules containing ~40% Methocel E4M (batch 0573/2012) and 50% Methocel E4M (batch 0576/2012) were manufactured and compressed into ~60N tablets (batches 0575/2012 and 0578/2012 respectively). The dissolution profiles of the granules and the corresponding tablets exhibited a better retard effect with the increased amount of Methocel E4M. However the differences in profile shapes and rates between tablets containing 40% and 50% were not significant. The release rate during the first hours was decreased in comparison to previous tablets containing 30% of the polymer (batch 0556/2012) but was however still slightly too fast.

We selected the formulation containing 30% Methocel E4M (reference batches 0548/2012 for the granules and 0556/2012 for the derived tablets) because of the appropriate profile obtained in this case (~85% release after 12H). Moreover it was assumed that the further IR buspirone coating to be applied on the zolmitriptan tablets will contribute to slow down the CR zolmitriptan rate during the first release hours (see next section concerning the development of the buspirone IR coating).

The pre-clinical prototype (granules batch 0590/2012 and corresponding tablets batch 0613/2012) was manufactured with the same method and process parameters that were used for the selected reference batches 0548/2012 (granules) and 0556/2012 (tablets). The pre-clinical prototype granules exhibited a Gaussian PSD with a D50-110 μm.

Development of the Buspirone HCl IR Coating:

The development of the buspirone IR coating was carried out in parallel to the development the CR zolmitriptan matrix tablets.

The first coating pre-trials were performed using placebo tablets (batch 0408/2012) in order to select the appropriate process parameters to be used during the further coating trials. The first pre-trial batch (0475/2012) was manufactured by spraying a placebo coating solution of Pharmacoat 603 on 500 g placebo tablets (batch 0408/2012).

The process was reproduced (batch 0476/2012) this time with buspirone dissolved together with Pharmacoat 603 in the coating solution. The solution was sprayed until the theoretical coated tablet weight was reached (before the drying step). The assay (relative to theory) from the obtained coated placebo tablets batch 0476/2012 was slightly below 95%. In order to improve the assay value, the same process was performed again with an excess of 5% coating solution applied after reaching the final targeted weight (batch 0477/2012). Despite this change the assay result was not further improved (assay relative to theory just below 93%). The assays from batches 0476/2012 and 0477/2012 were deemed satisfying at this stage of the product development.

The impact of a Pharmacoat 603 coating film on the release profile of the zolmitriptan tablets manufactured previously was investigated along with the feasibility of a coating batch size reduction during the same processes (batch size reduction down to 110 g).

Two different placebo coating processes (batches 0584/2012 and 0585/2012) were performed by applying a Pharmacoat 603 solution on zolmitriptan tablets (respectively on tablets batch 0554/2012 containing 25% Methocel E4M and on tablets batch 0556/2012 containing 30% Methocel E4M). As it can be seen on FIG. 6 the placebo coated zolmitriptan tablets batch 0585/2012 exhibited a slightly more retarded profile compared to the corresponding uncoated tablets (batch 0556/2012).

Figure 6:
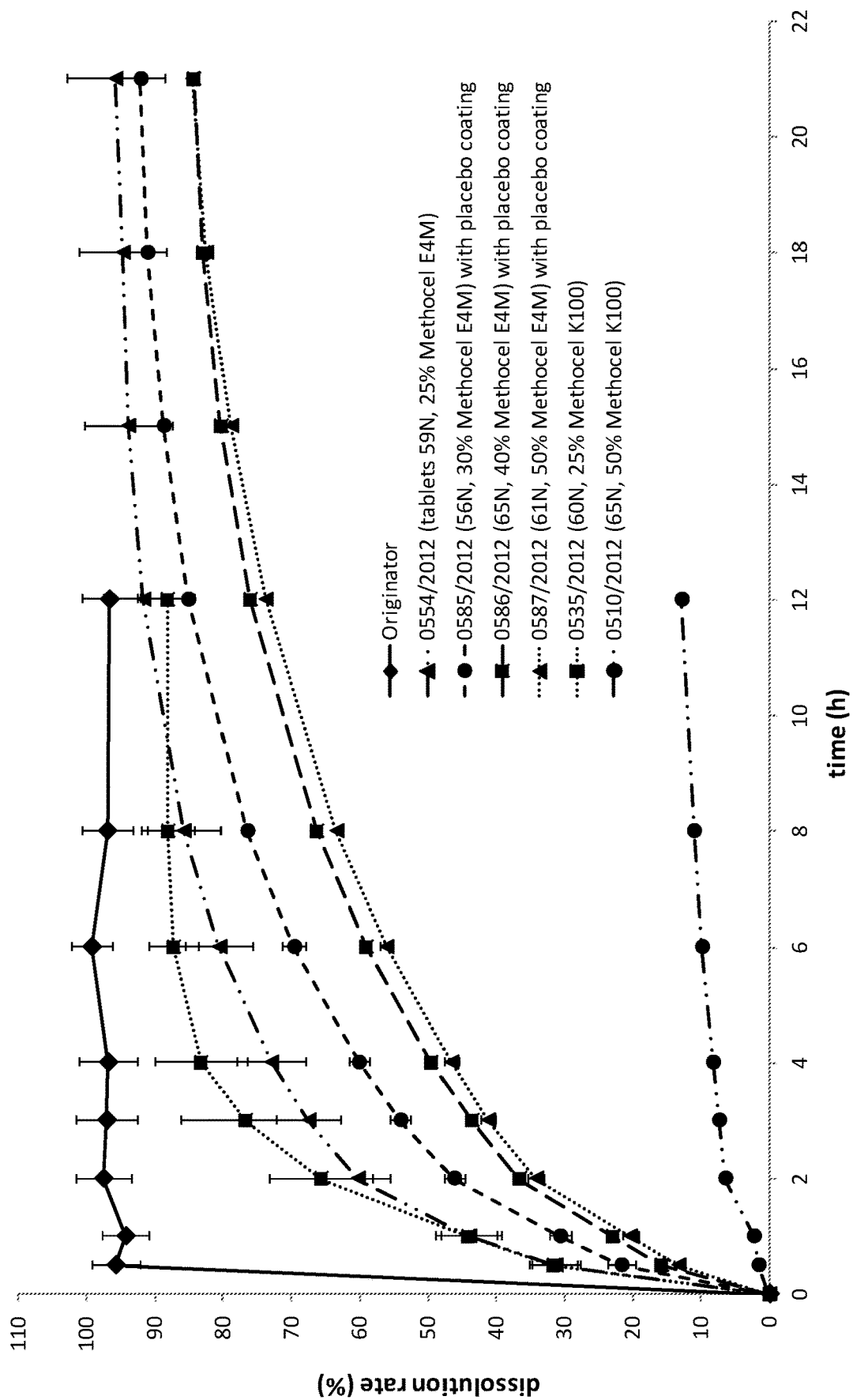
FIG. 6: Dissolution profiles of the current marketed tablet comprising zolmitriptan alone ('originator') for comparison and the produced zolmitriptan tablets compressed at a similar hardness (56N-65N) containing Methocel EM4 with or without a placebo coating, or Methocel K100 without coating. Numbers (e.g. 0554/2012) refer to internal batch number (see Example IX). Dissolution rate % refers to amount of active pharmaceutical ingredient released in a dissolution assay. The figure shows that the extended release properties of zolmitriptan can be designed to fit the most optimal (flat) pharmacokinetic profile of zolmitriptan.

The same placebo coating formulation was applied on zolmitriptan tablets batches 0575/2012 and 0578/2012 but with a starting batch size of 240 g. Indeed this quantity corresponds to the expected amount of zolmitriptan pre-clinical tablets which will be available for buspirone coating. As expected the resulting coated tablets obtained (batches 0586/2012 and 0587/2012 respectively) exhibited as well a slightly shifted release profile due to the HPMC coating (FIG. 6).

For the pre-clinical tablets coating process (batch 0614/2012) a reproduction of the previous process (batch 0587/2012) was carried out this time with the addition of buspirone HCl in the coating solution. The buspirone/Pharmacoat 603 solution was applied on 240 g of the pre-clinical zolmitriptan tablets (batch 0613/2012) until the targeted coated tablet weight was obtained (before the drying step). An overage corresponding to 10% of the previously applied quantity was additionally sprayed on the tablets afterwards before drying.

Figure 7:
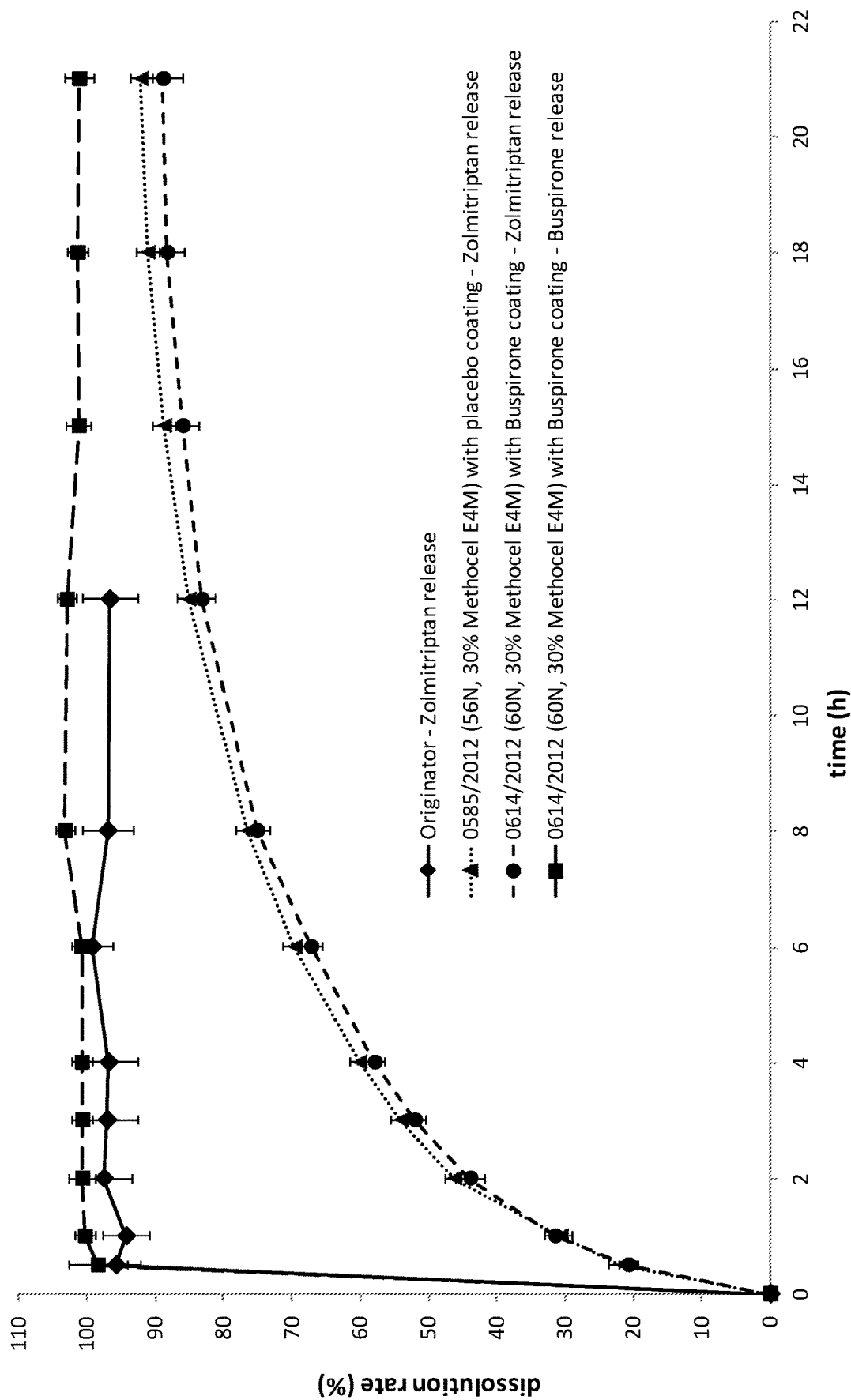
FIG. 7: Dissolution profiles of the zolmitriptan tablets containing Methocel EM4 with a buspirone coating (60N) (batch 0614/2012) showing the release pattern (dissolution rate) of each active ingredient; compared to the current marketed tablet comprising zolmitriptan alone ('originator') and a zolmitriptan tablet with a placebo coating. Dissolution rate % refers to amount of active pharmaceutical ingredient released in a dissolution assay. The figure shows that different dissolution patterns of zolmitriptan and buspirone are achieved when combined in the same tablet (batch 0614/2012). See Example X.

The APIs dissolution profiles of the final pre-clinical prototype (i.e. zolmitriptan 1 mg CR matrix tablets with buspirone 10 mg IR coating; 0614/2012-60N 30% Methocel EM4) exhibited satisfying release rates. As it can be seen in FIG. 7 the zolmitripan release rate was very similar to the one of the reference batch 0585/2012 (containing 30% Methocel E4M) with 83% release after 12H (85% release after 12H in the case of batch 0585/2012). For buspirone the release rate was very fast and consequently appropriate (98.5% after 30 min.). The assay value relative to theory were respectively 101.4% (RSD 2.07%) for buspirone HCl and 87.43% for zolmitriptan (RSD 0.10%).

Dissolution Method:

Online-UV, for Tablets Containing Only Buspirone or Zolmitriptan

Medium volume: 500 ml (acidic stage), ca. 655 ml (buffer-stage)

Dissolution time: up to 21 hrs (1 hour in 0.1 M HCl-solution followed by 20 hours in Phosphate buffer pH 6.8)

Sampling: after 0.5, 1, 2, 3, 4, 6, 8, 12, 15, 18 and 21 hours

Stirrer speed: 100 UPM

Apparatus: Paddles (Apparatus 2 USP) with sinker

Cuvette size: 1 cm

Wavelength: 225 nm

Temperature: 37° C.±0.5° C.

Filter system: Sartorius Glassfibre Prefilter

Offline-HPLC for Buspirone and Zolmitriptan Containing Tablets

Medium volume: 500 ml (acidic stage), ca. 655 ml (buffer-stage)

Dissolution time: up to 21 hrs (1 hour in 0.1 M HCl-solution followed by 20 hours in Phosphate buffer pH 6,8)

Sampling: after 0.5, 1, 2, 3, 4, 6, 8, 12, 15, 18 and 21 hours

Stirrer speed: 100 UPM

Apparatus: Paddles (Apparatus 2 USP) with sinker

Temperature: 37° C.±0.5° C.

Filter system: Sartorius Glassfibre Prefilter

HPLC-Method: see assay method for buspirone and/or zolmitriptan containing tablets, injection volume changed to 30 μl for Dissolution samples Assay Method for Buspirone and/or Zolmitriptan Containing Tablets:
A comparable and qualified system can be used.
Pump: Agilent 1100/1200 Quaternary pump
Injection system: Agilent 1100/1200 Autosampler with Rheodyne injection valve
Column oven: Agilent 1100/1200
Detector: Agilent 1100/1200 DAD
Software: Waters Empower 2
Parameters:
Method: Gradient
Column dimension: 250×4.6 mm
Stationary phase: Phenomenex Luna C18(2), 5 μm
Flowrate: 2.0 ml/min
Column temperature: 20° C.
Injection volume: 5 μl
Detection wavelength: 225 nm (width 4 nm)
Runtime: 12 min
Autosampler-temperature: 6° C.
Mobile phase A: 40 mM Phosphatpuffer pH 2.0
Mobile phase B: 100% Acetonitril
Gradient:

| Time [Min.] | Mobile phase A [%] | Mobile phase B [%] |
|---|---|---|
| 0 | 95 | 5 |
| 2 | 95 | 5 |
| 7 | 5 | 95 |
| 9 | 95 | 5 |
| 12 | 95 | 5 |

Retention time Zolmitriptan: approx. 5 min
Retention time Buspirone: approx. 6 min Example XI Manufacturing of a Fixed Dose Combination Product The manufacturing process for the pre-clinical prototype (i.e. zolmitriptan 1 mg CR matrix tablets with buspirone 10 mg IR coating; 0614/2012) is illustrated in FIG. 8 and described in detail herein below.
Granulation:
Equipment: GPCG1 (Glatt Powder Coater Granulator), Top-spray
Filter: PACF,
Bottom plate: standard PZ 100
Nozzle: 1.2 mm
Tube diameter inside/wall thickness: 3.2 mm×2.4 mm (silicon)
Filter shaking interval [sec]: 5
Filter shaking period [sec]: 5
Spray-Solution Preparation:
The Methocel K 100 was dissolved in water and stirred until a clear solution was obtained. Zolmitriptan was added to the previous solution and stirred until a homogeneous suspension was obtained.
Granulation Process:
The granulation was performed by spraying the Zolmitriptan suspension 65 min at a spray rate of 5.6-6.3 g/min and a product temperature of ~30° C. After spraying the appropriate suspension amount, the granules were dried during ~15 min. at a product temperature of ~40° C. until an LOD (loss on drying) ~2% was obtained

| Excipients | Lot no. | Amount % | Mass g | Mass (+10%) g |
|---|---|---|---|---|
| Solid starting material | | | | |
| Methocel E4M | W005847 | 31.07 | 177.074 | — |
| Avicel PH 101 | W005817 | 67.72 | 386.000 | — |
| Spraying liquid | | | | |
| Methocel E4M | W005847 | 0.51 | 2.926 | 3.219 |
| Zolmitriptan | W005806 | 0.70 | 4.000 | 4.400 |
| Pur. Water | | | 332.853 | 366.138 |
| Total spraying liquid (g) | | | 346.300 | 380.930 |
| Total solids (g) | | | 570.000 | — |
| Solids in spr. liq. (g) | | | 6.926 | 7.619 |
| Solids in spr.liq. (%) | | | 2.00 | 2.00 |

Blending and Compression:
Equipment: Tabletting machine: Fette P1200
Punches: 7.5 mm concave (3 punches installed)
Pre-compression force: 0.8 kN
Rotor speed: 21 rpm
Compression force: 9.3 kN
Target hardness of the tablets: 60N
Blending:
500 g of the zolmitriptan granules batch 0590/2012 were blended for 5 min with 5 g talc (ratio 95/5).

| Excipients | Lot no. | Amount % | Mass g |
|---|---|---|---|
| Solid starting material | | | |
| Zolmitriptan granules | 0590/2012 | 95.00 | 500.00 |
| Talc | W005811 | 5.00 | 26.316 |
| Total (g) | | | 526.31 |

Compression Process:
The blend (batch 0612/2012) was compressed into tablets (batch 0613/2012) at a hardness of 59-60 N. The tablet weight was controlled using 20 units. The mean tablet weight was 149.02-152,86 mg (rel. std.: 1.19%-2.45%).
Coating:
Equipment: GMPC 1 (Glatt Multi-Pan Coater), 0.8 L drum
Nozzle: 0.8 mm
Position of control screw: standard
Distance of nozzles to core bed: standard
Tube diameter inside/wall thickness: 1.6 mm×1.6 mm (silicon)
Pump: Periflow
Spray-Solution Preparation:
The Pharmacoat 603 was dissolved with dissolving disk and stirred until a clear solution was obtained. The buspirone HCl was dissolved in the previous solution with dissolving disk and stirred until clear solution was obtained.

| Excipients | Lot no. | Amount % | Mass g | Mass (+230%) g |
|---|---|---|---|---|
| Solid starting material | | | | |
| Placebo tablets (1 tab. = 151.60 mg) | 0613/2012 | 91.00 | 240.000 | |
| Spraying liquid | | | | |
| Pharmacoat 603 (33.33% = 5 mg/tab.) | W005808 | 3.00 | 7.916 | 18.207 |
| Buspirone HCl sieved (66.67% = 10 | W005829 | 6.00 | 15.831 | 36.411 |
| Purified water | | | 134.564 | 309.497 |
| Total spraying liquid (g) | | | 158.311 | 364.115 |
| Total solids (g) | | | 263.747 | — |
| Solids in spr. liq. (g) | | | 23.747 | 54.618 |
| Solids in spr.liq. (%) | | | 15.00 | 15.00 |

Coating Process:
  Mean tablet weight measured before coating: 150.47 mg
  Theoretical amount solid to apply: 15 mg (5 mg HPMC, 10 mg buspirone)
  Theoretical target weight of the tablet (batch 0614/2012) after coating process: 165.47 mg
  The buspirone solution was sprayed until the target tablet weight was weighed (202.5 g solution was sprayed). Then 10% of the amount sprayed previously was sprayed additionally (20.25 g additionally sprayed, total solution sprayed of 222.75 g). The final tablet weight after spraying was 166.03 mg which went down to 165.69 mg after drying step.

Example XII

In Vivo Evaluation of the Fixed Dose Combination Product

The present study describes the pharmacokinetic (PK) profiles of the buspirone (IR—immediate release)/zolmitriptan (CR—controlled release) 10 mg/1 mg combination product (batch 0614/2012; cf. Examples X and XI) in cynomolgus monkeys.

Test Procedure:
  Four non-naïve male cynomolgus monkeys (3.5 to 7 kg; Hainan Jingang Laboratory Animal Co. Ltd.) were used to evaluate the pharmacokinetics of the fixed dose combination product of the present invention. Animals were individually housed in stainless-steel mesh cages during in-life in accordance with the National Research Council "Guide for the Care and Use of Laboratory Animals" and fed twice daily with 120 g of Certified Monkey Diet daily (Beijing Vital Keao Feed Co., Ltd. Beijing, P. R. China). At test occasion, animals were fed the day before at 3:30 to 4:00 pm and the remaining food removed after approximately 1 to 1.5 hours of feeding (at 5:00 pm). Food was withheld until 4-hour post-dosage. The study was conducted in compliance with the Animal Welfare Act, the Guide for the Care and Use of Laboratory Animals, and the Office of Laboratory Animal Welfare (OLAW).

Each monkey was dosed one buspirone hydrochloride (IR)/zolmitriptan (CR) 10 mg/1 mg combination product (batch 0614/2012) orally using tablet gun, placing one tablet beyond the root of tongue. Subsequently, the animals' throat was massaged to aid passage of the tablet down the esophagus and 5-10 mL drinking water injected into its mouth using a syringe. After administration of drinking water, the animals' jaw was checked to see if the tablet was swallowed.

Blood samples were draw from a peripheral vessel from restrained, non-sedated animals at the following time points: pre-dose, 15, 30, 60 min, 2, 4, 8, 12 and 24 h post-dose into ($K_2$) EDTA-coated tubes. Plasma was obtained from the blood samples by centrifugation (3,000×g for 10 minutes at 2 to 8° C.) within one hour of collection and stored frozen in a freezer at −70° C. until bio-analysis.

Bioanalysis
  Analytes were extracted from plasma by mixing 200 μL 0.1% formic acid (FA) in 50% acetonitrile (ACN)/methanol (MeOH) containing 100 ng/mL Labetalol as internal standard with 50 μL plasma sample, followed by centrifugation (4000 rpm for 20 min).
  Subsequently, 100 μL of supernatant was removed and mixed with 150 μL 0.1% FA in 25% MeOH/Water, vortexed 10 min and centrifuged for 10 min at 4000 rpm. Chromatographic separation from other constituents of the sample was achieved by ultra-performance liquid chromatography (Acquity, Waters), followed by tandem mass spectrometry (MS/MS) detection (API 4000, AB Sciex Instruments), injecting 20 μL sample. The analytes were separated by an ACE 5 phenyl (2.1×100 mm ID) column maintained at 40° C., using a gradient of A: 10 mM ammonium acetate in water and solvent B: 0.1% FA in 95% ACN)/water (table 4).

TABLE 4

Gradient for chromatographic separation of buspirone and zolmitriptan.

| Time (min) | Flow Rate (mL/min) | % A | % B |
|---|---|---|---|
| Initial | 0.45 | 85 | 15 |
| 0.9 | 0.45 | 65 | 35 |
| 2.8 | 0.45 | 60 | 40 |
| 3.1 | 0.5 | 15 | 85 |
| 3.3 | 0.5 | 15 | 85 |
| 3.31 | 0.5 | 85 | 15 |
| 4.2 | 0.5 | 85 | 15 |

Solvent A: 10 mM ammonium acetate in water;
solvent B: 0.1% FA in 95% ACN/water

Ionisation of analytes was achieved with turbo ion spray in positive ion mode with selected reaction monitoring mode (MRM). Buspirone, zolmitriptan and labetalol were detected at parent/daughter molecular mass of 386.10/122.20, 288.10/58.20 and 329.20/161.90 m/z, and a collision energy of 41, 25 and 50 eV, respectively. Retention times were 2.3, 1.3 and 2.0 min for buspirone, zolmitriptan and labetalol, respectively. Peak areas correlated linearly ($r^2 > 0.997$, $1/x^2$ weighting) with buspirone and zolmitriptan concentrations in the range 0.5-1000 ng/mL. Lower limit of quantification (LLOQ) was 0.5 ng/mL for buspirone and zolmitriptan based on a signal-to-noise ratio>10:1.

Pharmacokinetic Analysis
  The PK analysis was performed with non-linear mixed effects modelling using Phoenix NMLE 1.2 (Pharsight Corporation). A one- or two-compartment model with first-order absorption and elimination rate was fitted to the time-concentration profiles. Furthermore, model development included modelling of the data with an absorption lag-time (Tlag). To adequately characterise a potential lag-time, the plasma concentrations<LLOQ (Lower Limit of Quantification) was fixed to ½ of LLOQ (0.25 ng/mL) for the sample just prior to the first quantifiable concentration. Best model fit was evaluated based on basic goodness-of-fit plots, parameter precision, visual predictive check and objective function value. A drop in objective function value of 3.74 for nested models with one added parameter was considered a significant improvement in model fit.

Results

Figure 9:
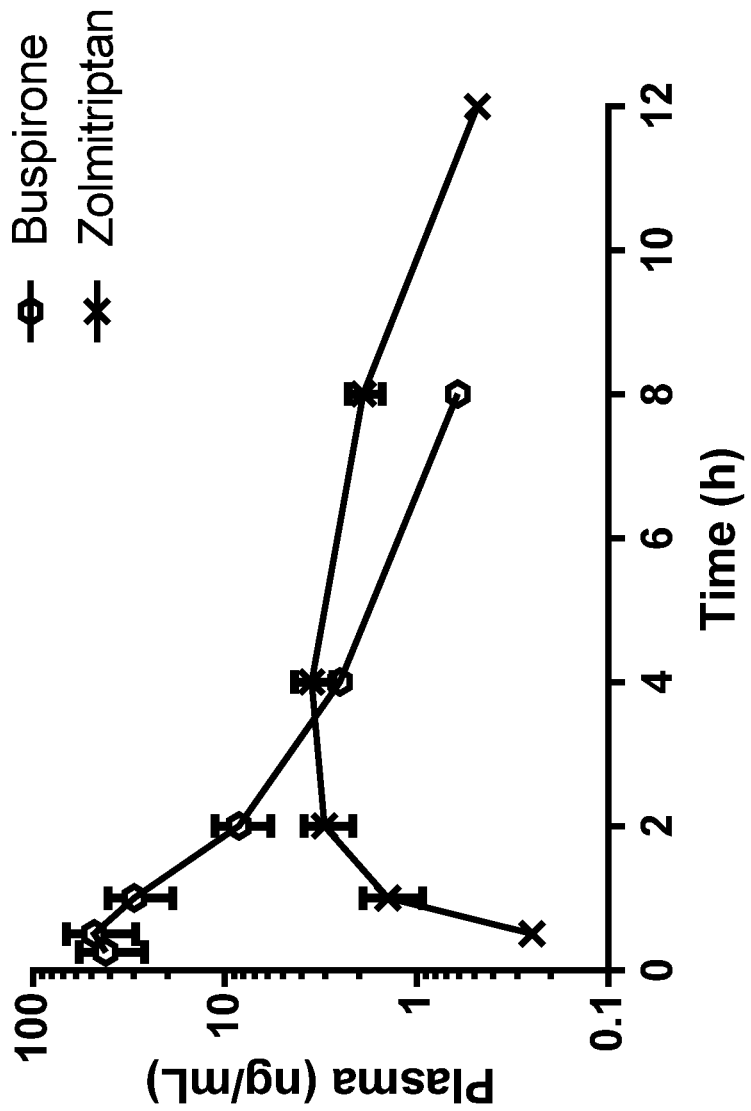
FIG. 9: Pharmacokinetic profiling of the combination formulation. Mean±sem (n=4) plasma concentration-time profile of buspirone and zolmitriptan in cynomolgus monkeys following oral administration of buspirone hydrochloride (IR)/zolmitriptan (CR) 10 mg/1 mg combination product (batch 0612/2012). See Example XII. CR=controlled release; IR=immediate release.

The plasma concentration-time profile of buspirone and zolmitriptan in monkeys following oral administration of the pharmaceutical formulation combination product comprising buspirone (IR) and zolmitriptan (CR) 10 mg/1 mg (batch 0614/2012) is presented in FIG. 9.

The pharmacokinetic profiles of each of the drugs are consistent with an immediate release and rapid absorption of buspirone with a maximum plasma concentration of buspirone around 0.5 h, and a subsequent slow controlled release of zolmitriptan with maximum plasma concentration of zolmitriptan at 4 h, that is sustained for 12 h above limit of quantification.

Non-linear mixed effects modelling suggested that the plasma concentration-time profile of buspirone in the monkeys was best described by a 2 compartment model with first-order absorption without lag-time. Inclusion of inter-individual variability (IIV) on clearance (CL) and absorption rate constant (ka) significantly improved the model fit. The residual unexplained variability was best described with a proportional error model. The plasma concentration-time profile of zolmitriptan was best described with a 1 compartment model with a first-order absorption rate and lag-time. IIV on volume of distribution (V) significantly improved parameter precision. The residual unexplained variability was best described with a proportional error model. Typical mean pharmacokinetic parameter values for the monkeys and IIV is collected in table 5. Consistent with FIG. 9, the model suggests a significant absorption lag-time for zolmitriptan of 0.44 h with no observable lag-time for buspirone. Furthermore, the absorption rate is suggested to be 3-fold slower for zolmitriptan compared to buspirone.

TABLE 5

Typical mean values (tv) of pharmacokinetic parameters and precision of estimates from non-linear mixed effects modelling of buspirone and zolmitriptan in cynomolgus monkeys following oral administration of Buspirone hydrochloride (IR)/ zolmitriptan (CR) 10 mg/1 mg combination product (batch 0614/2012)

| Parameter | Buspirone (% CV) | Zolmitriptan (% CV) |
|---|---|---|
| tvka (h$^{-1}$) | 1.0 (13) | 0.32 (55) |
| tvTlag (h) | — | 0.44 (3.8) |
| tyCL/F (L/h/kg) | 13 (124) | 7.0 (11) |
| tvV/F (L/kg) | 3.9 (26) | 16 (62) |
| tvQ/F (L/h/kg) | 18 (11) | — |
| tvV2/F (L/kg) | 1259 (29) | — |
| V/F IIV (%) | — | 0.1 |
| ka IIV (%) | 5.4 | — |
| CL/F IIV (%) | 37 | — |
| σ, prop | 0.17 (20) | 0.36 (21) | ka: absorption rate;
Tlag: absorption lag-time;
CL: clearance;
V: volume of central compartment;
V2: volume of peripheral compartment;
Q: inter-compartmental clearance;
F: bioavailability;
σ, prop: proportional residual unexplained variability;
IIV: inter-individual variability;
tv: typical value

The invention claimed is:

1. A pharmaceutical formulation comprising
   a. a matrix constituent comprising zolmitriptan, and pharmaceutically acceptable derivatives thereof, said matrix constituent providing for extended release of said zolmitriptan, and
   b. a constituent comprising buspirone, and pharmaceutically acceptable derivatives thereof, said constituent providing for immediate release of said buspirone.

2. The pharmaceutical formulation according to claim 1, wherein said formulation is a solid dosage form.

3. The pharmaceutical formulation according to claim 1, wherein said formulation comprises matrix constituent a. providing for extended release of zolmitriptan, and constituent b. providing for immediate release of buspirone, in separate compartments or layers.

4. The pharmaceutical formulation according to claim 1, wherein said formulation comprises
   a. an inner core matrix providing for extended release of zolmitriptan, and
   b. an outer coating providing for immediate release of buspirone.

5. The pharmaceutical formulation according to claim 1, wherein said formulation is a bi-layered tablet comprising
   a. one layer providing for extended release of zolmitriptan, and
   b. another layer providing for immediate release of buspirone,
   wherein each layer is present within the same tablet.

6. The pharmaceutical formulation according to claim 1, wherein each of said constituents a. and b. are provided together in a capsule, wherein said capsule comprises constituents a. and b. as separate granules or pellets.

7. The pharmaceutical formulation according to claim 1, wherein said matrix constituent a. and matrix constituent b. each comprises one or more excipients.

8. The pharmaceutical formulation according to claim 1, wherein said matrix constituent a. comprises one or more release-controlling excipients.

9. The pharmaceutical formulation according to claim 7, wherein said matrix constituent a. comprises the excipients hydroxypropylmethylcellulose (HPMC) and/or microcrystalline cellulose (MCC).

10. The pharmaceutical formulation according to claim 9, wherein said HPMC excipient is present in an amount of from 20-50%.

11. The pharmaceutical formulation according to claim 9, wherein said MCC excipient is present in an amount of from 50 to 80%.

12. The pharmaceutical formulation according to claim 1, wherein said matrix constituent a. further comprises talc.

13. The pharmaceutical formulation according to claim 12, wherein said talc is present in an amount of from 1-10%.

14. The pharmaceutical formulation according to claim 1, wherein said matrix constituent a. is compressed to a hardness of from 50-70N.

15. The pharmaceutical formulation according to claim 1, wherein said matrix constituent a. provides for at least 80% release of the zolmitriptan after 12 hours.

16. The pharmaceutical formulation according to claim 1, wherein said formulation comprises said zolmitriptan in an amount of from 0.1 to 10 mg.

17. The pharmaceutical formulation according to claim 1, wherein said matrix constituent a. consists of one or more HPMCs, one or more MCCs, talc, and zolmitriptan.

18. The pharmaceutical formulation according to claim 1, wherein said matrix constituent a. comprises or consists essentially of:
   a. 10-50% of HPMC,
   b. 40-80% of MCC,
   c. 1-10% of talc,
   d. 0.1-5% of zolmitriptan.

19. The pharmaceutical formulation according to claim 1, wherein said formulation comprises said buspirone in an amount of from 1 to 20 mg.

20. The pharmaceutical formulation according to claim 1, wherein said constituent b. comprises an excipient.

21. The pharmaceutical formulation according to claim 1, wherein said constituent b. comprises a film-forming excipient.

22. The pharmaceutical formulation according to claim 20, wherein said constituent b. excipient is a hydroxypropylmethylcellulose (HPMC).

23. The pharmaceutical formulation according to claim 1, wherein said constituent b. comprises or consists of at least one HPMC and buspirone.

24. The pharmaceutical formulation according to claim 1, wherein said constituent b. comprises or consists of:
   a. 25-40% HPMC
   b. 60-75% of buspirone.

25. The pharmaceutical formulation according to claim 1, wherein the formulation consisting of constituents a. and b. comprises or consists essentially of:
   a. 20-40% HPMC,
   b. 50-70% MCC,
   c. 1-10% of Talc,
   d. 0.1-10% of zolmitriptan,
   e. 1-20% of buspirone,
   f. 0.1-10% HPMC,
   wherein components a., b., c. and d. are comprised in matrix constituent a., and components e. and f. are comprised in constituent b.

26. The pharmaceutical formulation according to claim 1, wherein said formulation comprises one or more further active ingredients.

27. The pharmaceutical formulation according to claim 26, wherein said further active ingredient is selected form the group consisting of dopamine; dopamine prodrugs decarboxylase inhibitors; dopamine receptor agonists; NMDA antagonists; catechol-O-methyl transferases; COMT inhibitors; MAO-B inhibitors; serotonin receptor modulators; kappa opioid receptors agonists; GABA modulators; modulators of neuronal potassium channels; and glutamate receptor modulators.

28. The pharmaceutical formulation according to claim 27, wherein said further active ingredient is a dopamine prodrug.

29. The pharmaceutical formulation according to claim 1, wherein said formulation is for oral administration.

30. The pharmaceutical formulation according to claim 1, wherein said formulation is for use in the treatment of a movement disorder.

31. The pharmaceutical formulation according to claim 30, wherein said movement disorder is selected from the group of consisting of Parkinson's disease, movement disorders associated with Parkinson's disease, L-DOPA induced dyskinesia, tardive dyskinesia, ataxia, akathisia, dystonia, essential tremor, Huntington's disease, myoclonus, Rett syndrome, Tourette syndrome, Wilson's disease, dyskinesias, chorea, Machado-Joseph disease, restless leg syndrome, spasmodic torticollis, geniospasm or movement disorders associated therewith, movement disorders associated with use of drugs, idiopathic disease, genetic dysfunctions, infections or other conditions which lead to dysfunction of the basal ganglia and/or lead to altered synaptic dopamine levels, and withdrawal of drugs.

32. The pharmaceutical formulation according to claim 1, wherein said zolmitriptan is to be administered in a dosage of from 0.001 to 10 mg/kg bodyweight.

33. The pharmaceutical formulation according to claim 1, wherein said buspirone is to be administered in a dosage of from 0.01 to 10 mg/kg bodyweight.

34. The pharmaceutical formulation according to claim 1, wherein said formulation is to be administered once daily.

35. The pharmaceutical formulation according to claim 1, wherein said formulation is to be administered in combination with a separate dopamine prodrug, sequentially or simultaneously.

36. The pharmaceutical formulation according to claim 35, wherein said pharmaceutical formulation is administered before or simultaneously with a dopamine prodrug.

37. The pharmaceutical formulation according to claim 35, wherein said separate dopamine prodrug, is administered in combination with henzerazide.

38. The pharmaceutical formulation according to claim 1, wherein said formulation is to be administered as long as a movement disorder or an increased risk of developing a movement disorder is present.

39. The pharmaceutical formulation according to claim 1, wherein said formulation is manufactured by:
   1) preparing granules by mixing (MCC and HPMC) with (HPMC and the zolmitriptan),
   2) blending the granules of step 1) with talc,
   3) compressing the talc granules of step 2) into a matrix tablet,
   4) coating the matrix tablet of step 3) with a solution of (HPMC and buspirone), and
   5) drying the coated matrix tablet of step 4).

* * * * *